United States Patent
Smith et al.

(10) Patent No.: US 9,741,742 B2
(45) Date of Patent: Aug. 22, 2017

(54) DEFORMABLE ELECTRONIC DEVICE AND METHODS OF PROVIDING AND USING DEFORMABLE ELECTRONIC DEVICE

(71) Applicants: Joseph Smith, Tempe, AZ (US); Emmett Howard, Tempe, AZ (US); Jennifer Blain Christen, Chandler, AZ (US)

(72) Inventors: Joseph Smith, Tempe, AZ (US); Emmett Howard, Tempe, AZ (US); Jennifer Blain Christen, Chandler, AZ (US)

(73) Assignee: Arizona Board of Regents, a body corporate of the State of Arizona, acting for and on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/979,087

(22) Filed: Dec. 22, 2015

(65) Prior Publication Data
US 2016/0181288 A1  Jun. 23, 2016

Related U.S. Application Data

(60) Provisional application No. 62/095,579, filed on Dec. 22, 2014, provisional application No. 62/115,233, filed on Feb. 12, 2015.

(51) Int. Cl.
*H01L 21/44* (2006.01)
*H01L 27/12* (2006.01)
(Continued)

(52) U.S. Cl.
CPC .... *H01L 27/1218* (2013.01); *H01L 21/30604* (2013.01); *H01L 21/6835* (2013.01);
(Continued)

(58) Field of Classification Search
CPC .......... H01L 27/1218; H01L 21/76877; H01L 21/30604; H01L 29/78603; H01L 23/4985;
(Continued)

(56) References Cited

U.S. PATENT DOCUMENTS

| 3,089,801 A | 5/1963 | Tierney et al. |
| 3,684,637 A | 8/1972 | Andersen et al. |

(Continued)

FOREIGN PATENT DOCUMENTS

| CN | 1332599 | 1/2002 |
| CN | 1118075 | 8/2003 |

(Continued)

OTHER PUBLICATIONS

R. Lujan and R. A. Street, Oxide TFTs for a flexible x-ray image sensor. Palo Alto Research Center. Flex Tech Alliance Presents: Metal Oxide TFT Devices and Technology Workshop (Jul. 2012).

(Continued)

*Primary Examiner* — Thinh T Nguyen
(74) *Attorney, Agent, or Firm* — Bryan Cave LLP

(57) ABSTRACT

Some embodiments include a method of providing an electronic device. The method includes: (i) providing a carrier substrate, (ii) providing a device substrate comprising a first side and a second side opposite the first side, the device substrate having a flexible substrate, (iii) coupling the first side of the device substrate to the carrier substrate; and (iv) after coupling the first side of the device substrate to the carrier substrate, providing two or more active sections over the second side of the device substrate, each active section of the two or more active sections being spatially separate from each other and having at least one semiconductor device. Other embodiments of related methods and devices are also disclosed.

13 Claims, 12 Drawing Sheets

(51) Int. Cl.
*H01L 21/306* (2006.01)
*H01L 29/786* (2006.01)
*H01L 23/498* (2006.01)
*H01L 21/683* (2006.01)
*H01L 21/768* (2006.01)
*H01L 27/146* (2006.01)
*H01L 27/15* (2006.01)
*H01L 23/31* (2006.01)
*H01L 23/15* (2006.01)

(52) U.S. Cl.
CPC ........ *H01L 21/768* (2013.01); *H01L 23/3192* (2013.01); *H01L 23/4985* (2013.01); *H01L 27/1262* (2013.01); *H01L 27/14636* (2013.01); *H01L 27/153* (2013.01); *H01L 29/78603* (2013.01); *A61B 2562/02* (2013.01); *A61B 2562/164* (2013.01); *H01L 23/15* (2013.01); *H01L 2221/6835* (2013.01); *H01L 2221/68381* (2013.01); *H01L 2924/0002* (2013.01)

(58) Field of Classification Search
CPC ............... H01L 27/1262; H01L 23/291; H01L 23/3171; H01L 23/5226; H01L 23/528; H01L 21/6835; H01L 2221/68359
USPC ............... 438/149, 151, 666, 158, 159, 161; 257/57, 59, 60, 72
See application file for complete search history.

(56) References Cited

U.S. PATENT DOCUMENTS

| | | |
|---|---|---|
| 3,723,635 A | 3/1973 | Smith |
| 4,337,107 A | 6/1982 | Eshleman |
| 4,349,593 A | 9/1982 | Blechstein |
| 4,489,487 A | 12/1984 | Bura |
| 4,858,073 A | 8/1989 | Gregory |
| 5,098,772 A | 3/1992 | af Strom |
| 5,117,114 A | 5/1992 | Street et al. |
| 5,220,488 A | 6/1993 | Denes |
| 5,229,882 A | 7/1993 | Rowland |
| 5,252,383 A | 10/1993 | Fukutake et al. |
| 5,264,063 A | 11/1993 | Martin |
| 5,292,686 A | 3/1994 | Riley et al. |
| 5,453,157 A | 9/1995 | Jeng |
| 5,702,980 A | 12/1997 | Yu et al. |
| 5,714,305 A | 2/1998 | Teng et al. |
| 5,853,511 A | 12/1998 | Fairbanks |
| 5,861,470 A | 1/1999 | Voss et al. |
| 5,869,150 A | 2/1999 | Iwamoto |
| 5,890,429 A | 4/1999 | Alam et al. |
| 5,916,652 A | 6/1999 | Miner et al. |
| 6,051,169 A | 4/2000 | Brown et al. |
| 6,051,508 A | 4/2000 | Takase et al. |
| 6,083,580 A | 7/2000 | Finestone et al. |
| 6,177,163 B1 | 1/2001 | Blok et al. |
| 6,358,832 B1 | 3/2002 | Edelstein et al. |
| 6,482,288 B1 | 11/2002 | Kreckel et al. |
| 6,531,389 B1 | 3/2003 | Shue et al. |
| 6,541,398 B2 | 4/2003 | Grill et al. |
| 6,580,035 B1 | 6/2003 | Chung |
| 6,627,037 B1 | 9/2003 | Kurokawa et al. |
| 6,630,289 B1 | 10/2003 | Kwok et al. |
| 6,632,746 B2 | 10/2003 | Kanegae et al. |
| 6,670,265 B2 | 12/2003 | Wang et al. |
| 6,746,969 B2 | 6/2004 | Shimada et al. |
| 6,752,160 B2 | 6/2004 | Chen |
| 6,808,773 B2 | 10/2004 | Shimamura et al. |
| 6,825,068 B2 | 11/2004 | Denis et al. |
| 6,856,670 B2 | 2/2005 | Hoheisel |
| 7,212,088 B1 | 5/2007 | Norregaard et al. |
| 7,316,942 B2 | 1/2008 | Sarma et al. |
| 7,329,601 B2 | 2/2008 | Miyajima |
| 7,344,993 B2 | 3/2008 | Balasubramaniam et al. |
| 7,375,341 B1 | 5/2008 | Nagarkar et al. |
| 7,385,224 B2 | 6/2008 | Ishii et al. |
| 7,481,901 B2 | 1/2009 | Toyoda et al. |
| 7,538,038 B2 | 5/2009 | Matsushita et al. |
| 7,563,026 B2 | 7/2009 | Mandelkern et al. |
| 7,795,006 B2 | 9/2010 | Nagino et al. |
| 7,838,328 B2 | 11/2010 | Isa |
| 7,906,193 B2 | 3/2011 | Yukawa et al. |
| 8,038,820 B2 | 10/2011 | Kim et al. |
| 8,048,251 B2 | 11/2011 | Yamashita et al. |
| 8,383,520 B2 | 2/2013 | Marrs |
| 8,481,859 B2 | 7/2013 | Haq et al. |
| 8,992,712 B2 | 3/2015 | Loy et al. |
| 8,999,778 B2 * | 4/2015 | O'Rourke ........... H01L 21/6835 257/59 |
| 9,076,822 B2 * | 7/2015 | Loy ..................... H01L 21/6835 |
| 2002/0008839 A1 | 1/2002 | Miyai et al. |
| 2002/0018173 A1 | 2/2002 | Furukawa et al. |
| 2002/0081863 A1 | 6/2002 | Shimada et al. |
| 2003/0031296 A1 | 2/2003 | Hoheisel |
| 2003/0069331 A1 | 4/2003 | Teiichi et al. |
| 2003/0072889 A1 | 4/2003 | Abrams |
| 2003/0201465 A1 | 10/2003 | Ryuzaki et al. |
| 2004/0008298 A1 | 1/2004 | Kwok et al. |
| 2004/0110326 A1 | 6/2004 | Forbes et al. |
| 2005/0186801 A1 | 8/2005 | Uno et al. |
| 2005/0221542 A1 | 10/2005 | Yamazaki et al. |
| 2005/0221599 A1 | 10/2005 | Kanegae et al. |
| 2005/0233583 A1 | 10/2005 | Miyajima |
| 2005/0242341 A1 | 11/2005 | Knudson et al. |
| 2006/0017154 A1 | 1/2006 | Eguchi et al. |
| 2006/0019491 A1 | 1/2006 | Soda |
| 2006/0148141 A1 | 7/2006 | Seo et al. |
| 2006/0169485 A1 | 8/2006 | Kawaguchi et al. |
| 2006/0180815 A1 | 8/2006 | Sarma et al. |
| 2006/0192229 A1 | 8/2006 | Kato et al. |
| 2006/0194363 A1 | 8/2006 | Giesberg et al. |
| 2006/0207967 A1 | 9/2006 | Bocko et al. |
| 2006/0223282 A1 | 10/2006 | Amundson et al. |
| 2007/0054440 A1 | 3/2007 | Hu |
| 2007/0241436 A1 | 10/2007 | Ookubo et al. |
| 2008/0038885 A1 | 2/2008 | Lee et al. |
| 2008/0050548 A1 | 2/2008 | Abrams |
| 2008/0090338 A1 | 4/2008 | Tredwell et al. |
| 2008/0105877 A1 | 5/2008 | Yamazaki et al. |
| 2008/0122121 A1 | 5/2008 | Suda et al. |
| 2008/0179594 A1 | 7/2008 | Oh |
| 2008/0224243 A1 | 9/2008 | Lee |
| 2008/0315252 A1 | 12/2008 | Shim |
| 2009/0004419 A1 | 1/2009 | Cok et al. |
| 2009/0008132 A1 | 1/2009 | Takasawa et al. |
| 2009/0072122 A1 | 3/2009 | Tada et al. |
| 2009/0101903 A1 | 4/2009 | Chen et al. |
| 2009/0134390 A1 | 5/2009 | Kodama et al. |
| 2009/0202857 A1 | 8/2009 | Kerr et al. |
| 2009/0211791 A1 | 8/2009 | Tredwell et al. |
| 2009/0229874 A1 | 9/2009 | Katagiri et al. |
| 2009/0269874 A1 | 10/2009 | Huang et al. |
| 2009/0294767 A1 | 12/2009 | Lujan et al. |
| 2009/0296754 A1 | 12/2009 | Ledentsov et al. |
| 2010/0003512 A1 | 1/2010 | Ookubo et al. |
| 2010/0003513 A1 | 1/2010 | Ookubo et al. |
| 2010/0025675 A1 | 2/2010 | Yamazki et al. |
| 2010/0038023 A1 | 2/2010 | Kho et al. |
| 2010/0051189 A1 | 3/2010 | Kawabata et al. |
| 2010/0059171 A1 | 3/2010 | Chun et al. |
| 2010/0059747 A1 | 3/2010 | Nakayama et al. |
| 2010/0123131 A1 | 5/2010 | Tokunaga |
| 2010/0140807 A1 | 6/2010 | Kobayashi et al. |
| 2010/0154992 A1 | 6/2010 | Feinstein et al. |
| 2010/0155694 A1 | 6/2010 | Miller et al. |
| 2010/0183872 A1 | 7/2010 | Nonaka et al. |
| 2010/0203296 A1 | 8/2010 | Tsai et al. |
| 2010/0219410 A1 | 9/2010 | Godo et al. |
| 2010/0267203 A1 | 10/2010 | Chen et al. |
| 2010/0295161 A1 | 11/2010 | Koduri |
| 2010/0330748 A1 | 12/2010 | Chu et al. |
| 2011/0003442 A1 | 1/2011 | Wang et al. |
| 2011/0048611 A1 | 3/2011 | Carre et al. |

(56) References Cited

U.S. PATENT DOCUMENTS

| | | | |
|---|---|---|---|
| 2011/0064953 A1 | 3/2011 | O'Rourke et al. |
| 2011/0069467 A1 | 3/2011 | Flaim et al. |
| 2011/0111194 A1 | 5/2011 | Carre et al. |
| 2011/0141076 A1 | 6/2011 | Fukuhara et al. |
| 2011/0141476 A1 | 6/2011 | Schmaelzle et al. |
| 2011/0227203 A1 | 9/2011 | Marrs et al. |
| 2011/0228492 A1 | 9/2011 | Haq et al. |
| 2011/0240988 A1 | 10/2011 | Yano |
| 2011/0318544 A1 | 12/2011 | Chen et al. |
| 2012/0061672 A1* | 3/2012 | O'Rourke | H01L 21/6835 257/57 |
| 2012/0107978 A1 | 5/2012 | Shin et al. |
| 2012/0146713 A1 | 6/2012 | Kim et al. |
| 2012/0164408 A1 | 6/2012 | Hwu et al. |
| 2012/0168836 A1 | 7/2012 | Lee et al. |
| 2012/0300419 A1 | 11/2012 | Tang et al. |
| 2012/0329249 A1 | 12/2012 | Ahn et al. |
| 2013/0075739 A1* | 3/2013 | Loy | H01L 21/6835 257/60 |
| 2013/0077033 A1 | 3/2013 | Li et al. |
| 2014/0008651 A1 | 1/2014 | Marrs |
| 2014/0254113 A1 | 9/2014 | Howard et al. |
| 2014/0340857 A1 | 11/2014 | Hsu et al. |
| 2015/0064385 A1 | 3/2015 | Flaim et al. |
| 2015/0097301 A1 | 4/2015 | Gandhi |
| 2015/0162392 A1 | 6/2015 | Lim et al. |
| 2016/0225653 A1 | 8/2016 | Marrs et al. |
| 2016/0260765 A1 | 9/2016 | Marrs |
| 2016/0260768 A1 | 9/2016 | Smith et al. |
| 2017/0062380 A1 | 3/2017 | Howard et al. |

FOREIGN PATENT DOCUMENTS

| | | |
|---|---|---|
| CN | 1454122 | 11/2003 |
| CN | 101231972 | 7/2007 |
| CN | 101288348 | 10/2008 |
| CN | 103531442 | 1/2014 |
| JP | 01198094 | 9/1989 |
| JP | 07022795 | 1/1995 |
| JP | 08148814 | 7/1996 |
| JP | 11340462 | 10/1999 |
| JP | 2000338454 | 12/2000 |
| JP | 2004311912 | 11/2004 |
| JP | 2004323543 | 11/2004 |
| JP | 2005123576 | 12/2005 |
| JP | 2007073559 | 3/2007 |
| JP | 2007123861 | 5/2007 |
| JP | 2007146121 | 6/2007 |
| JP | 200971057 | 4/2009 |
| JP | 2010067849 | 3/2010 |
| JP | 2010226101 | 10/2010 |
| JP | 2012212939 | 11/2012 |
| KR | 20070103050 | 10/2007 |
| KR | 100810708 | 3/2008 |
| KR | 1020090098033 | 9/2009 |
| KR | 1020100007703 | 1/2010 |
| KR | 1020100043654 | 4/2010 |
| KR | 1020130086807 | 8/2013 |
| WO | 9852391 | 11/1998 |
| WO | 2006088564 | 8/2006 |
| WO | 2007083906 | 7/2007 |
| WO | 2007108659 | 9/2007 |
| WO | 2008005979 | 1/2008 |
| WO | 2010051106 | 5/2010 |
| WO | 2010065542 | 6/2010 |
| WO | 2010138811 | 12/2010 |
| WO | 2014054949 | 4/2014 |
| WO | 2015058523 | 4/2015 |
| WO | 2015156891 | 10/2015 |
| WO | 2015175353 | 11/2015 |
| WO | 2017034644 | 3/2017 |
| WO | 2017034645 | 3/2017 |

OTHER PUBLICATIONS

R. A. Street, W. S. Wong, T. Ng & R. Lujan. Amorphous silicon thin film transistor image sensors, Philosophical Magazine, 89:28-30, 2687-2697 (Oct. 2009).

J. C. Park, S. Kim, S. Kim, C. Kim, I. Song, Y. Park, U. Jung, D. H. Kim, and J. Lee. Highly Stable Transparent Amorphous Oxide Semiconductor Thin-Film Transistors Having Double-Stacked Active Layers. Adv. Mater. 2010, 22, 5512-5516.

R. A. Lujan and R. A. Street. Flexible X-Ray Detector Array Fabricated With Oxide Thin-Film Transistors. IEEE Electron Device Letters, vol. 33, No. 5, May 2012.

International Search Report and Written Opinion from related Int'l Application No. PCT/US2015/029991 dated Jul. 31, 2015, 13 pages.

International Search Report and Written Opinion for Int'l Application No. PCT/US2014/060501, Jan. 19, 2015, 14 pages.

International Search Report and Written Opinion from related Int'l Application No. PCT/US2013/058284 dated Dec. 26, 2013, 12 pages.

International Search Report and Written Opinion from related Int'l Application No. PCT/US2013/058293 dated Dec. 26, 2013, 12 pages.

International Search Report and Written Opinion from related Int'l Application No. PCT/US2012/066833 dated Jan. 17, 2013, 11 pages.

International Search Report and Written Opinion from related Int'l Application No. PCT/US2011/037207 dated Feb. 21, 2012, 10 pages.

International Search Report and Written Opinion from related Int'l Application No. PCT/US2011/037226 dated Feb. 21, 2012, 10 pages.

International Search Report and Written Opinion from related Int'l Application No. PCT/US2012/032388 dated Dec. 10, 2012, 10 pages.

International Search Report and Written Opinion from related Int'l Application No. PCT/US2010/036569 dated Dec. 27, 2012, 11 pages.

International Search Report and Written Opinion from related Int'l Application No. PCT/US2009/066259 dated May 5, 2010, 8 pages.

International Search Report and Written Opinion from related Int'l Application No. PCT/US2009/066111 dated Oct. 25, 2010, 7 pages.

International Search Report and Written Opinion from related Int'l Application No. PCT/US2009/066114 dated Mar. 9, 2010, 8 pages.

International Search Report and Written Opinion for PCT/US2016/036505, dated Mar. 17, 2017.

International Search Report and Written Opinion for PCT/US2016/036502, dated Mar. 6, 2017.

\* cited by examiner

DEFORMABLE ELECTRONIC DEVICE AND METHODS OF PROVIDING AND USING DEFORMABLE ELECTRONIC DEVICE

CROSS-REFERENCE TO RELATED APPLICATIONS

This application claims the benefit of U.S. Provisional Patent Application No. 62/095,579, filed Dec. 22, 2014, and claims the benefit of U.S. Provisional Patent Application No. 62/115,233, filed Feb. 12, 2015. U.S. Provisional Patent Application No. 62/095,579 and U.S. Provisional Patent Application No. 62/115,233 are incorporated herein by reference in their entirety.

FIELD OF THE INVENTION

This invention relates generally to electronic devices, and relates more particularly to deformable (e.g., flexible and/or stretchable) electronic devices and methods of providing and using the same.

BACKGROUND OF THE INVENTION

Deformable (e.g., flexible and/or stretchable) device substrates, which can include a wide variety of materials, such as, for example, any of a myriad of plastics, metal foils, and glasses, are quickly becoming popular as a base for electronic devices. For example, deformable device substrates can provide an advantageous base for wearable consumer electronic devices.

Currently available wearable consumer electronic devices (e.g., chest strap or wrist-mounted fitness monitors) are expected to be developed into next generation wearable consumer electronic devices including bioelectronic sensors, closely coupled or integrated with the human anatomy to detect and/or diagnose multiple diseases in real-time, and with clinical level sensitivity. Exemplary next generation wearable consumer electronic devices can include transdermal electronic skin patches (i.e., smart bandages) that continuously monitor for disease state biomarkers in patients with common chronic conditions, such as diabetes, anemia, or heart disease. However, in order for such next generation wearable consumer electronic devices to make a successful transition from the research laboratory environment to market, production costs must be decreased and manufacturability must be increased. Most low cost, high volume consumer electronic devices are manufactured today using silicon wafer-based microelectronic components, printed circuit boards (PCBs), and glass substrate-based flat panel displays. However, these conventional electronic device manufacturing technologies are fundamentally rigid and/or planar, while biological surfaces and systems are traditionally soft and/or pliable. Accordingly, these inherent incompatibilities have prompted increased research in new deformable electronic device manufacturing technologies to produce the next generation of wearable consumer electronic devices.

Initial development efforts have focused primarily on manufacturing flexible electronic displays using flexible plastic device substrates. These large area flexible electronics displays have been shown to be slightly bendable but not stretchable. For wearable consumer electronic device applications, these flexible electronic displays can provide shatter resistance, which is helpful in diagnostic applications where sensors need to come in direct contact with organic tissue (e.g., skin, bodily organs, etc.) and/or with consumables, such as for water quality monitoring or food safety inspection.

Meanwhile, more recent development efforts have focused on manufacturing flexible electronic devices that are also stretchable. By making flexible electronic devices stretchable, such deformable electronic devices can conform to complex biological surfaces (e.g., organic tissue, etc.), and can be repeatedly deformed (e.g., flexed and/or stretched) without damage or loss of electronic device functionality. Examples of stretchable flexible electronic devices have been reported using stretchable conductive metal traces fabricated on deformable elastomeric plastic substrates. Generally, these stretchable flexible electronic devices have been manufactured by individually bonding discrete electronic components to the deformable elastomeric plastic substrates. However, these manufacturing approaches have failed to achieve the decreases in production costs and the increases in manufacturability that are needed to bring these deformable electronic devices (e.g., wearable consumer electronic devices) to market.

BRIEF DESCRIPTION OF THE DRAWINGS

To facilitate further description of the embodiments, the following drawings are provided in which.

Figure 1:
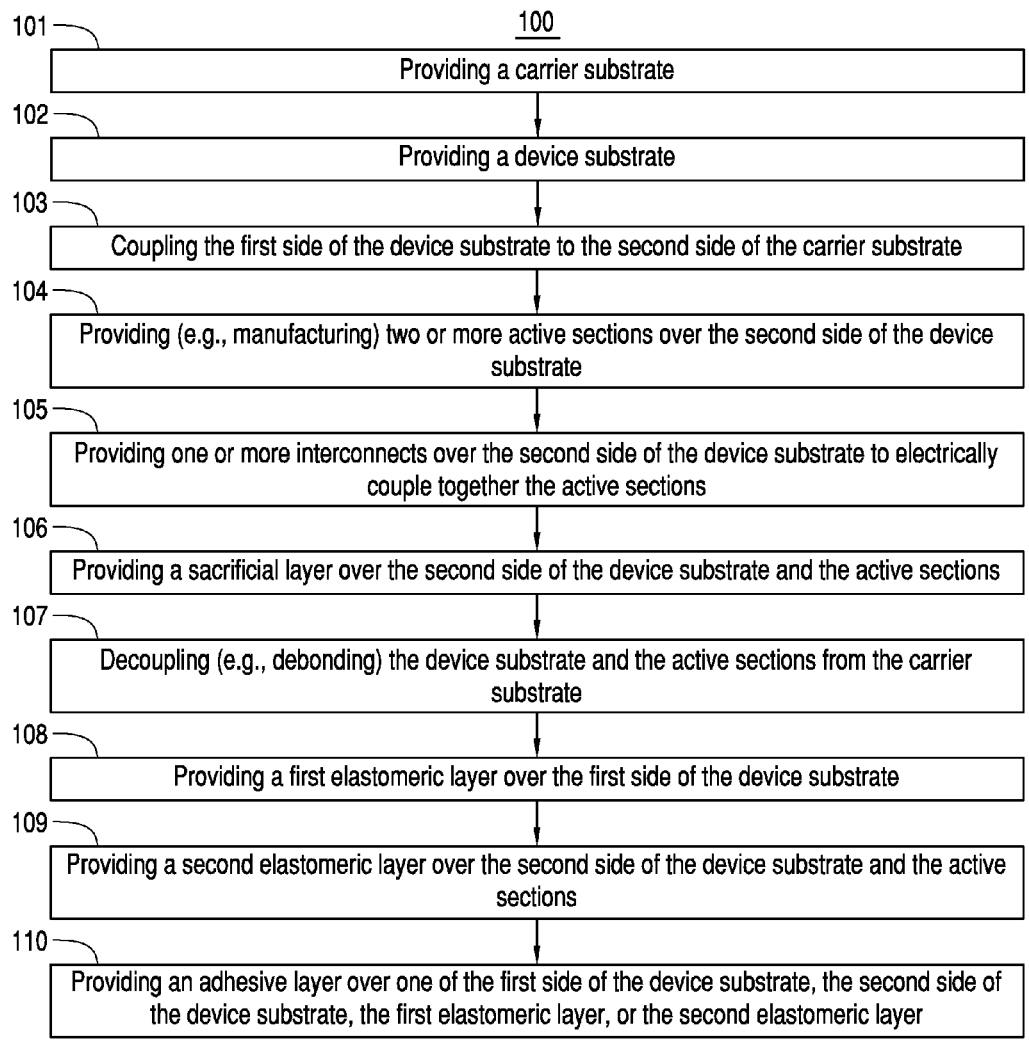
FIG. 1 illustrates an example of a method of providing an electronic device, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled together but not be mechanically or otherwise coupled together; two or more mechanical elements may be mechanically coupled together, but not be electrically or otherwise coupled together; two or more electrical elements may be mechanically coupled together, but not be electrically or otherwise coupled together. Coupling may be for any length of time, e.g., permanent or semi-permanent or only for an instant.

An electrical "coupling" and the like should be broadly understood and include coupling involving any electrical signal, whether a power signal, a data signal, and/or other types or combinations of electrical signals. A mechanical "coupling" and the like should be broadly understood and include mechanical coupling of all types.

The absence of the word "removably," "removable," and the like near the word "coupled," and the like does not mean that the coupling, etc. in question is or is not removable.

The term "bowing" as used herein means the curvature of a substrate about a median plane, which is parallel to the top and bottom sides, or major surfaces of the substrate. The term "warping" as used herein means the linear displacement of the surface of a substrate with respect to a z-axis, which is perpendicular to the top and bottom sides, or major surfaces of the substrate. The term "distortion" as used herein means the displacement of a substrate in-plane (i.e., the x-y plane, which is parallel to the top and bottom sides, or major surfaces of the substrate). For example, distortion could include shrinkage in the x-y plane of a substrate and/or expansion in the x-y plane of the substrate.

The term "CTE matched material" and the like as used herein means a material that has a coefficient of thermal expansion (CTE) which differs from the CTE of a reference material by less than about 20 percent (%). Preferably, the CTEs differ by less than about 10%, 5%, 3%, or 1%.

The term "flexible substrate" as used herein means a free-standing substrate that readily adapts its shape. Accordingly, in many embodiments, the flexible substrate can comprise (e.g., consist of) a flexible material, and/or can comprise a thickness (e.g., an average thickness) that is sufficiently thin so that the substrate readily adapts in shape. In these or other embodiments, a flexible material can refer to a material having a low elastic modulus. Further, a low elastic modulus can refer to an elastic modulus of less than approximately five GigaPascals (GPa). In some embodiments, a substrate that is a flexible substrate because it is sufficiently thin so that it readily adapts in shape, may not be a flexible substrate if implemented with a greater thickness, and/or the substrate may have an elastic modulus exceeding five GPa. For example, the elastic modulus could be greater than or equal to approximately five GPa but less than or equal to approximately twenty GPa, fifty GPa, seventy GPa, or eighty GPa. Exemplary materials for a substrate that is a flexible substrate because it is sufficiently thin so that it readily adapts in shape, but that may not be a flexible substrate if implemented with a greater thickness, can comprise certain glasses (e.g., fluorosilicate glass, borosilicate glass, Corning® glass, Willow™ glass, and/or Vitrelle glass, etc., such as, for example, as manufactured by Corning Inc. of Corning, N.Y., United States of America, etc.) or silicon having a thickness greater than or equal to approximately 25 micrometers and less than or equal to approximately 100 micrometers.

The terms "elastomeric substrate" and/or "elastomeric layer" as used herein can mean a layer comprising one or more materials, having the properties of a flexible substrate, and also having a high yield strength. That is, the elastomeric substrate and/or elastomeric layer is a free-standing layer that readily adapts its shape and that substantially recovers (e.g., with little or no plastic deformation) from applied stresses and/or strains. Because applied stresses and/or strains depend on environment and implementation, in exemplary embodiments, a high yield strength can refer to a yield strength greater than or equal to approximately 2.00 MegaPascals, 4.14 MegaPascals, 5.52 MegaPascals, and/or 6.89 MegaPascals.

Meanwhile, the term "rigid substrate" as used herein can mean a free-standing substrate that does not readily adapt its shape and/or a substrate that is not a flexible substrate. In some embodiments, the rigid substrate can be devoid of flexible material and/or can comprise a material having an elastic modulus greater than the elastic modulus of a flexible substrate. In various embodiments, the rigid substrate can be implemented with a thickness that is sufficiently thick so that the substrate does not readily adapt its shape. In these or other examples, the increase in rigidity of the carrier substrate provided by increasing the thickness of the carrier substrate can be balanced against the increase in cost and weight provided by increasing the thickness of the carrier substrate.

As used herein, "polish" can mean to lap and polish a surface or to only lap the surface.

DETAILED DESCRIPTION

Some embodiments include a method of providing an electronic device. The method comprises: providing a carrier substrate; providing a device substrate comprising a first side and a second side opposite the first side, the device substrate comprising a flexible substrate; coupling the first side of the device substrate to the carrier substrate; and after coupling the first side of the device substrate to the carrier substrate, providing two or more active sections over the second side of the device substrate, each active section of the two or more active sections being spatially separate from each other and comprising at least one semiconductor device.

Other embodiments include an electronic device. The electronic device comprises a device substrate comprising a first side and a second side opposite the first side. The device substrate can comprise a flexible substrate. Further, the electronic device comprises two or more active sections over the second side of the device substrate. Each active section of the two or more active sections can be spatially separate from each other and can comprise at least one semiconductor device. Further still, the electronic device can comprise one or more wavy metal interconnects over the second side of the device substrate electrically coupling together the two or more active sections.

Further embodiments include a method comprising: decoupling a sacrificial layer from an electronic device; and coupling the electronic device to organic tissue. The electronic device can comprise a device substrate comprising a first side and a second side opposite the first side. Meanwhile, the device substrate can comprise a flexible substrate. Further, the electronic device can comprise two or more active sections over the second side of the device substrate. Meanwhile, each active section of the two or more active sections can be spatially separate from each other and can comprise at least one semiconductor device. Further still, the electronic device can comprise one or more wavy metal interconnects over the second side of the device substrate electrically coupling together the two or more active sections, and the sacrificial layer over the second side of the device substrate and the two or more active sections.

Turning to the drawings, FIG. 1 illustrates an example of a method 100 of providing an electronic device, according to an embodiment. Method 100 is merely exemplary and is not limited to the embodiments presented herein. Method 100 can be employed in many different embodiments or examples not specifically depicted or described herein. In some embodiments, the activities of method 100 can be performed in the order presented. In other embodiments, the activities of method 100 can be performed in any other suitable order. In still other embodiments, one or more of the activities in method 100 can be combined or skipped. Although the electronic device can comprise any suitable electronic device, in many embodiments, the electronic device can comprise a wearable consumer electronic device (e.g., a transdermal smart bandage). Further, the electronic device (e.g., wearable consumer electronic device) can comprise one or more flat panel electronic displays, one or more bioelectronics devices (e.g., biological sensors), etc. In these or other embodiments, the electronic device can comprise a deformable electronic device. Accordingly, the electronic device can be flexible and/or stretchable. As discussed in greater detail herein, the flexibility and/or stretchability of the electronic device can depend on the material properties of the device substrate and/or the elastomeric layer implemented with the electronic device.

Figure 2:
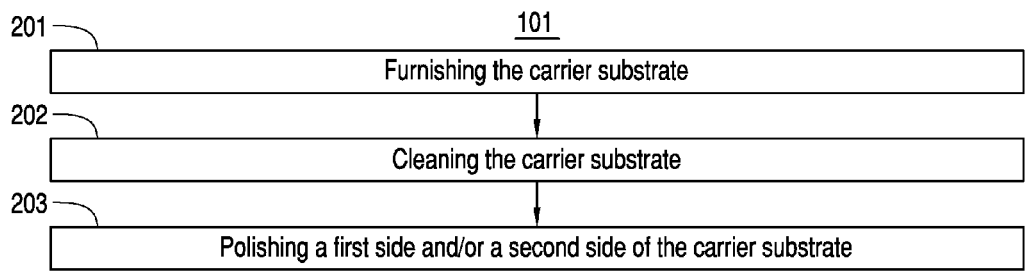
FIG. 2 illustrates an exemplary activity of providing a carrier substrate of the electronic device, according to the embodiment of FIG. 1.

Method 100 comprises activity 101 of providing a carrier substrate. FIG. 2 illustrates an exemplary activity 101, according to the embodiment of FIG. 1.

For example, activity 101 can comprise activity 201 of furnishing the carrier substrate. The carrier substrate can comprise a first side and a second side opposite the first side. The carrier substrate can be configured to minimize bowing, warping, and/or distortion of the device substrate when the device substrate is coupled to the carrier substrate, as described below.

In many embodiments, the carrier substrate can comprise a rigid substrate. The carrier substrate (e.g., rigid substrate) can comprise any suitable material(s) having the characteristics of a rigid substrate as defined above. Specifically, exemplary material(s) can comprise alumina ($Al_2O_3$), silicon, glass (e.g., barium borosilicate, soda lime silicate, and/or an alkali silicate), metal (e.g., steel, such as, for example, stainless steel), and/or sapphire. However, in some embodiments, the carrier substrate (e.g., rigid substrate) can be devoid of silicon and/or amorphous silicon. Meanwhile, in many embodiments, the glass can comprise a low CTE glass.

Further, material(s) for the carrier substrate (e.g., rigid substrate) also can be selected so that a CTE of the material(s) approximately matches a CTE of the material(s) of the device substrate, which is introduced briefly above and described in greater detail below. Likewise, in some embodiments, material(s) for the device substrate can be selected so as to be CTE matched with the material(s) of the carrier substrate. Non-matched CTEs can create stress between the carrier substrate and the device substrate, which can result in bowing, warping, and/or distortion of the device substrate when the device substrate is coupled to the carrier substrate.

Meanwhile, in many embodiments, the carrier substrate can be a wafer or panel. The wafer or panel can comprise any suitable dimensions (e.g., diameter, thickness, length, width, etc.), as applicable. In some embodiments, the wafer or panel can comprise a largest dimension (e.g., diameter, length) of approximately 6 inches (approximately 15.24 centimeters), approximately 8 inches (approximately 20.32 centimeters), approximately 12 inches (approximately 30.48 centimeters), or approximately 18 inches (approximately 45.72 centimeters). In some embodiments, the carrier substrate can be a panel of approximately 370 mm in width by approximately 470 mm in length. In some examples, the wafer or panel can comprise a thickness of at least approximately 0.5 millimeters.

Later, in some embodiments, activity 101 can comprise activity 202 of cleaning the carrier substrate. In some embodiments, activity 202 can be performed by cleaning the carrier substrate with plasma (e.g., oxygen plasma) or with an ultrasonic bath.

Then, activity 101 can comprise activity 203 of polishing a first side and/or a second side of the carrier substrate. Polishing the side of the carrier substrate (e.g., the first side) that is not subsequently coupled (e.g., bonded) with the device substrate, as described below, improves the ability of a vacuum or air chuck to handle the carrier substrate. Also, polishing the surface of the carrier substrate (e.g., the second side) that is subsequently coupled (e.g., bonded) to the device substrate, as described below, removes topological features at that side of the carrier substrate that could cause roughness of the resulting device substrate assembly in the z-axis after the device substrate and carrier substrate are coupled together.

Referring now back to FIG. 1, method 100 comprises activity 102 of providing a device substrate. Like the carrier substrate, the device substrate can comprise a first side and a second side opposite the first side. Activity 102 can be performed before, after, or approximately simultaneously with activity 101.

In many embodiments, the device substrate can comprise a flexible substrate. The device substrate (e.g., flexible substrate) can comprise any suitable material(s) having the characteristics of a flexible substrate as defined above. Specifically, exemplary material(s) can comprise polyethylene naphthalate, polyethylene terephthalate, polyethersulfone, polyimide, polycarbonate, cyclic olefin copolymer, liquid crystal polymer, any other suitable polymer, glass (e.g., fluorosilicate glass, borosilicate glass, Corning® glass, Willow™ glass, and/or Vitrelle glass, etc., such as, for example, as manufactured by Corning Inc. of Corning, N.Y., United States of America, etc.), metal foil (e.g., aluminum foil, etc.), etc. In these or other embodiments, the device substrate can comprise an elastic modulus of less than approximately five GigaPascals. Further, the device substrate can comprise a thickness of greater than or equal to approximately 1 micrometer and less than or equal to approximately 1 millimeter. In these or other embodiments, the thickness of the device substrate can be less than or equal to approximately 10 micrometers.

In many embodiments, activity 102 can comprise an activity of furnishing the device substrate. In some embodiments, activity 102 can comprise an activity of depositing the device substrate over the second side of the carrier substrate. In many embodiments, the depositing the device substrate over the second side of the carrier substrate can be performed using any suitable deposition technique(s) (e.g., chemical vapor deposition, such as, for example plasma-enhanced chemical vapor deposition, sputtering, molecular beam epitaxy, spin-coating, spray-coating, extrusion coating, preform lamination, slot die coating, screen lamination, and/or screen printing, etc.). For example, in some embodiments, the depositing the device substrate over the second side of the carrier substrate can be performed as described in International Patent Application No. PCT/US2015/029991, filed on May 8, 2015, which published as International Patent Application Publication No. WO/2015/175353 on Mar. 15, 2012. Accordingly, International Patent Application Publication No. WO/2015/175353 is incorporated by reference in its entirety. In these embodiments, activity 103 (below) can be performed as part of activity 102.

Figure 3:
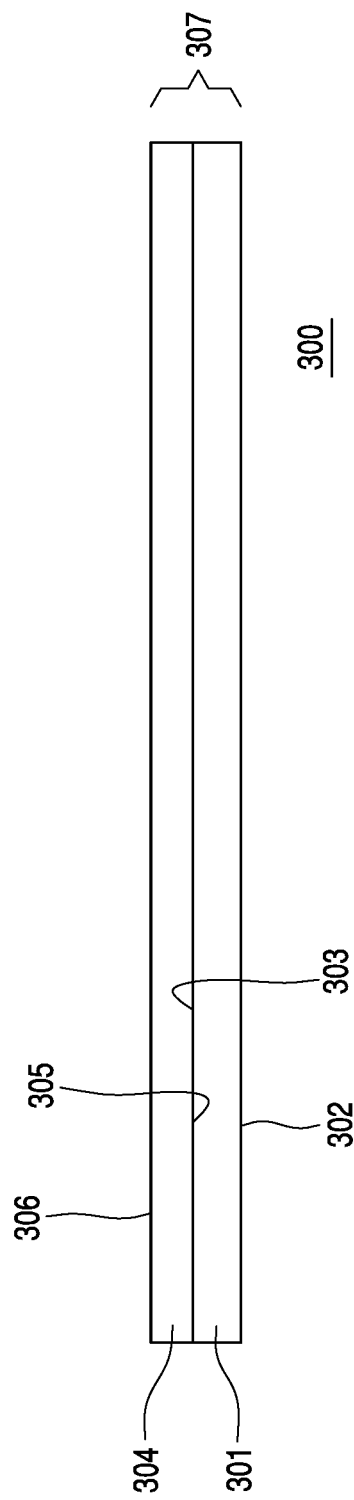
FIG. 3 illustrates a partial cross-sectional view of an electronic device after coupling a first side of a device substrate having the first side and a second side to the second side of a carrier substrate having a first side and the second side to provide a substrate assembly, according to the embodiment of FIG. 1.

Referring again to FIG. 1, method 100 comprises activity 103 of coupling the first side of the device substrate to the second side of the carrier substrate. Turning forward briefly in the drawings, FIG. 3 illustrates a partial cross-sectional view of an electronic device 300 after coupling a first side 305 of a device substrate 304 having the first side 305 and a second side 306 to the second side 303 of a carrier substrate 301 having a first side 302 and the second side 303 to provide substrate assembly 307, according to the embodiment of FIG. 1. In these or other embodiments, electronic device 300 can be similar or identical to the electronic device of method 100 (FIG. 1). Accordingly, device substrate 304 can be similar or identical to the device substrate of method 100 (FIG. 1), and carrier substrate 301 can be similar or identical to the carrier substrate of method 100 (FIG. 1).

Turning again to FIG. 1, in many embodiments, activity 103 is performed after activity 101. In these or other embodiments, activity 103 can be performed simultaneously with and/or after activity 102. In some embodiments, activity 103 can be performed as part of activity 102, as described above.

In various embodiments, performing activity 103 can comprise an activity of bonding the first side of the flexible substrate to the second side of the carrier substrate with an adhesive. The adhesive can be any suitable type of adhesive (e.g., a cross-linking adhesive). In many embodiments, the bonding the first side of the flexible substrate to the second side of the carrier substrate with the adhesive can be performed using any suitable bonding technique. For example, in some embodiments, the bonding the first side of the flexible substrate to the second side of the carrier substrate with the adhesive can be performed as described in any of (i) U.S. patent application Ser. No. 13/118,225, filed May 27, 2011, which issued as U.S. Pat. No. 8,481,859 on Jul. 9, 2013, (ii) U.S. patent application Ser. No. 13/298,451, filed Nov. 17, 2011, which issued as U.S. Pat. No. 8,999,778 on Apr. 7, 2015, (iii) U.S. patent application Ser. No. 13/683,950, filed Nov. 21, 2012, which issued as U.S. Pat. No. 8,992,712 on Mar. 31, 2015, (iv) U.S. patent application Ser. No. 14/288,771, filed May 28, 2014, which published as United States Patent Application Publication No. 2014/0254113 on Sep. 11, 2014, (v) International Patent Application No. PCT/US14/60501, filed on Oct. 14, 2014, which published as International Patent Application Publication No. WO/2015/057719 on Apr. 23, 2015, (vi) International Patent Application No. PCT/US15/12717, filed on Jan. 23, 2015, which published as International Patent Application Publication No. WO/2015/156891 on Oct. 15, 2015, and/or (vii) International Patent Application No. PCT/US15/29991, filed on May 8, 2015, which published as International Patent Application Publication No. WO/2015/175353 on Nov. 19, 2015. Accordingly, U.S. Pat. No. 8,481,859, U.S. Pat. No. 8,999,778, U.S. Pat. No. 8,992,712, United States Patent Application Publication No. 2014/0254113, International Patent Application Publication No. WO/2015/057719, International Patent Application Publication No. WO/2015/156891, and International Patent Application Publication No. WO/2015/175353 each are incorporated by reference in their entirety.

In other embodiments, performing activity 103 can comprise an activity of depositing the device substrate over the second side of the carrier substrate. In these embodiments, the activity of depositing the device substrate over the second side of the carrier substrate can be performed as described above with respect to activity 102.

In various embodiments, after activity 103 is performed, the device substrate can be cured (e.g., thermally cured), such as, for example, at a temperature of approximately 350° C.

Referring back to FIG. 1, method 100 comprises activity 104 of providing (e.g., manufacturing) two or more active sections over the second side of the device substrate. Notably, in many embodiments, each of the active sections can be provided (e.g., manufactured) approximately simultaneously with each other. Further, activity 104 can be performed after activity 103.

In these or other embodiments, the active sections can be arranged apart (e.g., spatially separate, isolated, etc.) from each other and/or each can comprise at least one semiconductor device. In essence, the active sections can comprise semiconductor device islands arranged over the second side of the device substrate. By arranging the active sections apart from each other over the device substrate, the electronic device can be deformable (e.g., flexible and/or stretchable), as discussed in greater detail below. As a result, the electronic device can be implemented as a wearable consumer electronic device able to conform with uneven and/or pliable surfaces (e.g., organic tissue, etc.).

In some embodiments, the active sections can be uniformly arranged over the device substrate, though other arrangements (e.g., random arrangements) can also be implemented. In some embodiments, two or more of the active sections can be similar or identical to each other. In these or other embodiments, two or more of the active sections can be different from each other.

As described in greater detail below, in many embodiments, activity 104 can be performed by providing excess active section material over the second side of the device substrate and removing (e.g., etching) part of the active section material so that the active sections remain, but in other embodiments, the active sections can be provided (e.g., manufactured) by selective deposition over the second side of the device substrate. However, in some examples, selective deposition may require performing additional manufacturing activities that may lead to increased manufacturing costs.

Advantageously, as explained in greater detail below, the active sections can be provided (e.g., manufactured) over the device substrate (e.g., flexible substrate) with direct integration rather than with a multi-stage process of providing the active sections over one or more other substrates and then transferring the active sections to the device substrate (e.g., flexible substrate). Moreover, as noted, the active sections can be provided (e.g., manufactured) approximately simultaneously so the need to systematically and/or individually couple (e.g., bond) each of the active sections to the device substrate (e.g., flexible substrate) can be avoided. These advantages can improve manufacturability and decrease manufacturing costs.

Further, many embodiments of method 100 can leverage the inherent scalability advantages of conventional flat panel electronic display manufacturing technologies, which currently use flexible substrates approaching lateral dimensions of approximately 10 square meters. Accordingly, un-functionalized manufacturing costs can be reduced, and because the flat panel electronic display industrial base is already well established and capable of annually supplying the electronic devices required to transition wearable consumer electronic devices from the laboratory to market. For perspective, flat panel electronic displays in 2012 were manufactured at a rate of 100 square kilometers per year. Accordingly, if just one percent (1%) of the existing flat panel electronic display industrial capacity was diverted to manufacture large area wearable consumer electronic devices, approximately seven hundred thousand people each year could be covered entirely from head to toe with wearable consumer electronic devices. Further, assuming an average area of twenty five square centimeters for each smart bandage, approximately four hundred million smart bandages could be manufactured annually.

Figure 4:
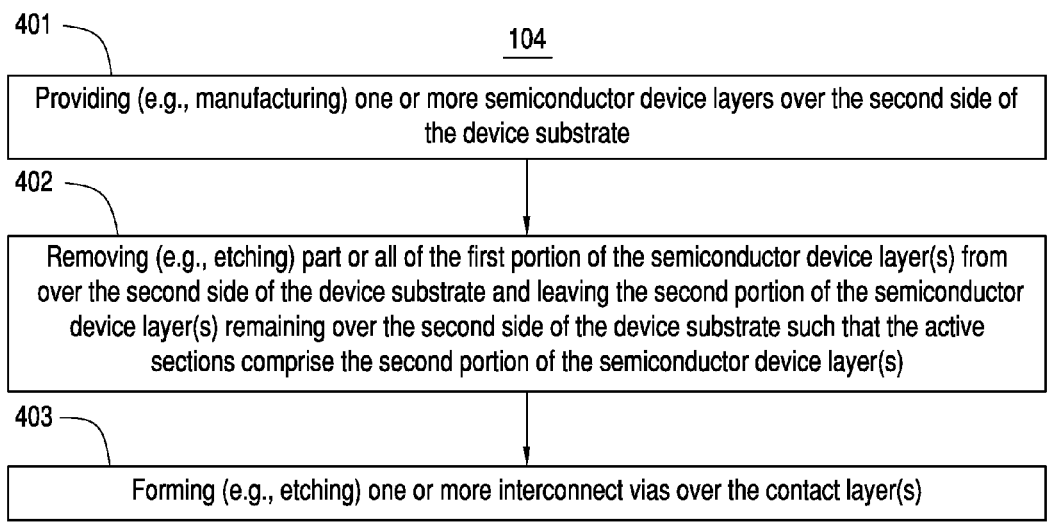
FIG. 4 illustrates an exemplary activity of providing (e.g., manufacturing) two or more active sections of the electronic device over a second side of a device substrate of the electronic device, according to the embodiment of FIG. 1.

Recognizing that method 100 can leverage conventional flat panel electronic display manufacturing techniques, FIG. 4 illustrates an exemplary activity 104, according to the embodiment of FIG. 1. To begin with, activity 104 can comprise activity 401 of providing (e.g., manufacturing) one or more semiconductor device layers over the second side of the device substrate. In general, activity 401 can be performed after activities 101-103. In many embodiments, the semiconductor device layer(s) can be provided (e.g., manufactured) over the second side of the device substrate by deposition. When the semiconductor device layer(s) are provided over the second side of the device substrate by deposition, the deposition can be performed using any suitable deposition technique(s) (e.g., chemical vapor deposition, such as, for example plasma-enhanced chemical vapor deposition, sputtering, molecular beam epitaxy, spin-coating, spray-coating, extrusion coating, preform lamination, slot die coating, screen lamination, and/or screen printing, etc.) and/or under any deposition condition(s) suitable for the material(s) elected for the first semiconductor device layer(s), the device substrate, and/or the carrier substrate.

For example, in these or other embodiments, the providing (e.g., manufacturing) one or more semiconductor device layers over the second side of the device substrate can be performed as described in any of (i) U.S. patent application Ser. No. 13/298,451, filed Nov. 17, 2011, which issued as U.S. Pat. No. 8,999,778 on Apr. 7, 2015, (ii) U.S. patent application Ser. No. 13/683,950, filed Nov. 21, 2012, which issued as U.S. Pat. No. 8,992,712 on Mar. 31, 2015, (iii) U.S. patent application Ser. No. 13/684,150, filed Nov. 21, 2012, which issued as U.S. Pat. No. 9,076,822 on Jul. 7, 2015, (iv) U.S. patent application Ser. No. 14/029,502, filed Sep. 17, 2013, which published as United States Patent Application Publication No. 2014/0008651 on Jan. 9, 2014, (v) U.S. patent application Ser. No. 14/288,771, filed May 28, 2014, which published as United States Patent Application Publication No. 2014/0254113 on Sep. 11, 2014, (vi) International Patent Application No. PCT/US13/58284, filed on Sep. 5, 2013, which published as International Patent Application Publication No. WO2014/039693 on Mar. 13, 2014, (vii) International Patent Application No. PCT/US14/60501, filed on Oct. 14, 2014, which published as International Patent Application Publication No. WO2015/057719 on Apr. 23, 2015, (viii) International Patent Application No. PCT/US15/12717, filed on Jan. 23, 2015, which published as International Patent Application Publication No. WO/2015/156891 on Oct. 15, 2015, and/or (ix) International Patent Application No. PCT/US15/29991, filed on May 8, 2015, which published as International Patent Application Publication No. WO/2015/175353 on Nov. 19, 2015. Accordingly, U.S. Pat. No. 8,999,778, U.S. Pat. No. 8,992,712, U.S. Pat. No. 9,076,822, United States Patent Application Publication No. 2014/0008651, United States Patent Application Publication No. 2014/0254113, International Patent Application Publication No. WO2014/039693, International Patent Application Publication No. WO2015/

057719, International Patent Application Publication No. WO/2015/156891, and International Patent Application Publication No. WO/2015/175353 each are incorporated by reference in their entirety. In further embodiments, the semiconductor device layer(s) can be provided (e.g., manufactured) over the second side of the device substrate with an electronics on plastic by laser release (EPLaR™) manufacturing technique. EPLaR™ manufacturing allows flexible thin film electronics (e.g., flat panel displays) to be fabricated using existing high temperature (e.g., greater than or equal to approximately 300° C.) commercial thin film electronics manufacturing process tooling and process steps.

Figure 5:
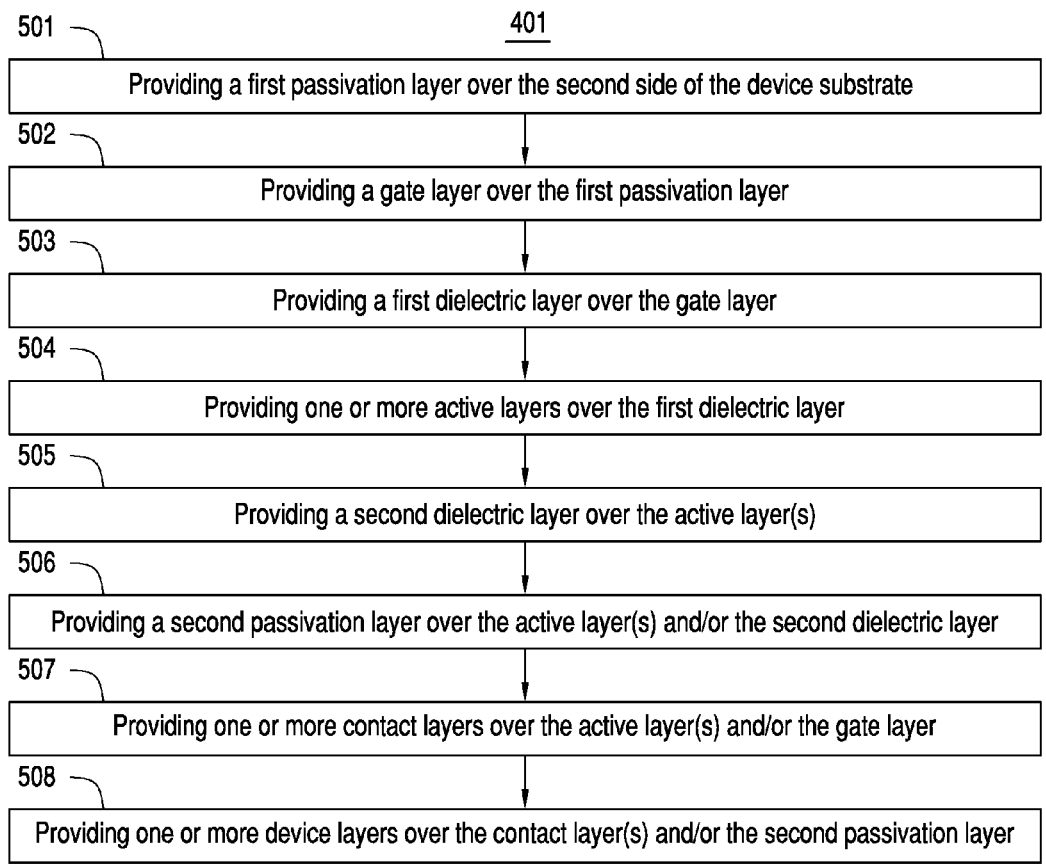
FIG. 5 illustrates an exemplary activity of providing (e.g., manufacturing) one or more semiconductor device layers of the electronic device over the second side of the device substrate, according to the embodiment of FIG. 1.

Turning to the next drawing, FIG. 5 illustrates an exemplary activity 401, according to the embodiment of FIG. 1. For example, activity 401 can comprise activity 501 of providing a first passivation layer over the second side of the device substrate. In many embodiments, the first passivation layer can comprise silicon nitride. However, any material(s) suitable to protect the device substrate during subsequent semiconductor manufacturing activities can be implemented. For example, the first passivation layer can be operable as a moisture barrier and/or a chemical barrier to protect the device substrate from the caustic chemicals used during activity 401.

Further, activity 401 can comprise activity 502 of providing a gate layer over the first passivation layer. The gate layer can comprise a conductive material. For example, in many embodiments, the conductive material can comprise molybdenum and/or aluminum.

Further, activity 401 can comprise activity 503 of providing a first dielectric layer over the gate layer. In many embodiments, the first dielectric layer can comprise silicon nitride. Other dielectric materials can also be implemented.

Further, activity 401 can comprise activity 504 of providing one or more active layers over the first dielectric layer. In many embodiments, the active layer(s) can comprise amorphous silicon and/or one or more metal oxides (e.g., indium oxide, zinc oxide, gallium oxide, tin oxide, hafnium oxide, aluminum oxide, etc.).

Further, activity 401 can comprise activity 505 of providing a second dielectric layer over the active layer(s). In many embodiments, the second dielectric layer can comprise silicon nitride. Other dielectric materials can also be implemented.

Further, activity 401 can comprise activity 506 of providing a second passivation layer over the active layer(s) and/or the second dielectric layer. In many embodiments, the second passivation layer can comprise silicon nitride.

Figure 6:
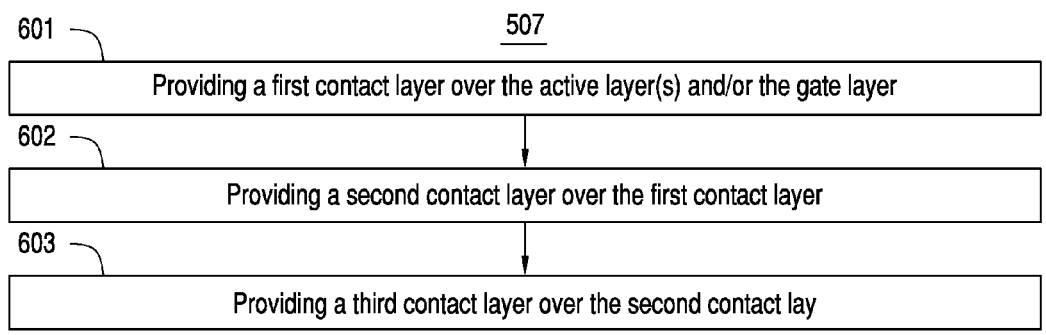
FIG. 6 illustrates an exemplary activity of providing one or more contact layers of the semiconductor layer(s) over one or more active layer and/or a gate layer of the semiconductor layers, according to the embodiment of FIG. 1.

Further, activity 401 can comprise activity 507 of providing one or more contact layers over the active layer(s) and/or the gate layer. FIG. 6 illustrates an exemplary activity 507, according to the embodiment of FIG. 1.

For example, activity 507 can comprise activity 601 of providing a first contact layer over the active layer(s) and/or the gate layer. In many embodiments, the first contact layer can comprise N+ amorphous silicon.

Further, activity 507 can comprise activity 602 of providing a second contact layer over the first contact layer. In many embodiments, the second contact layer can be configured to prevent movement by diffusion of atoms from a third contact layer (below) into the first contact layer. According, in some embodiments, the second contact layer can comprise tantalum.

Further, activity 507 can comprise activity 603 of providing a third contact layer over the second contact layer. The third contact layer can comprise a conductive material. Exemplary conductive materials can comprise molybdenum and/or aluminum.

Turning now back to FIG. 5, activity 401 can comprise activity 508 of providing one or more device layers over the contact layer(s) and/or the second passivation layer. In these or other embodiments, the various layer(s) provided in activities 501-507 can provide one or more thin film transistors, and the device layer(s) can provide one or more electronic components (e.g., electronic emitters, sensors, etc.) coupled to the thin film transistor(s). Together, the thin film transistor(s) and the electronic component(s) can comprise the semiconductor device(s) of the active sections of method 100 (FIG. 1) and/or activity 104 (FIG. 1).

Notably, in many embodiments, one or more of activity 401 (FIG. 4), activities 501-508 and/or activities 601-603 (FIG. 6) can comprise one or more patterning activities in which the various layers of activities 501-508 and/or activities 601-603 can be patterned, as desirable. These patterning activities can be performed using conventional semiconductor patterning techniques and/or the patterning activities described in one or more of U.S. patent application Ser. No. 13/298,451, U.S. patent application Ser. No. 13/683,950, U.S. patent application Ser. No. 13/684,150, U.S. patent application Ser. No. 14/029,502, U.S. patent application Ser. No. 14/288,771, International Patent Application No. PCT/US13/58284, International Patent Application No. PCT/US14/60501, U.S. Provisional Patent Application No. 61/930,853, U.S. Provisional Patent Application No. 61/992,799.

Figure 7:
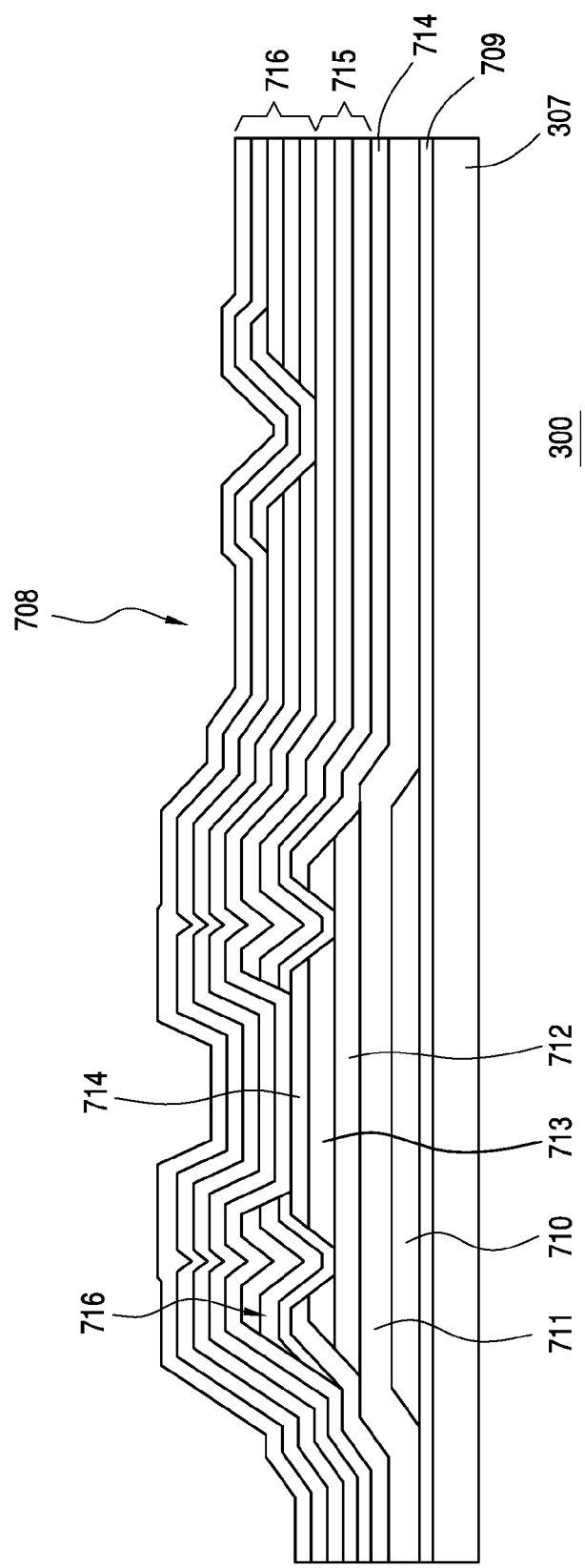
FIG. 7 illustrates a partial cross-sectional view of the electronic device of FIG. 3 in a device build area of the electronic device after providing one or more semiconductor device layers over the substrate assembly.
Figure 8:
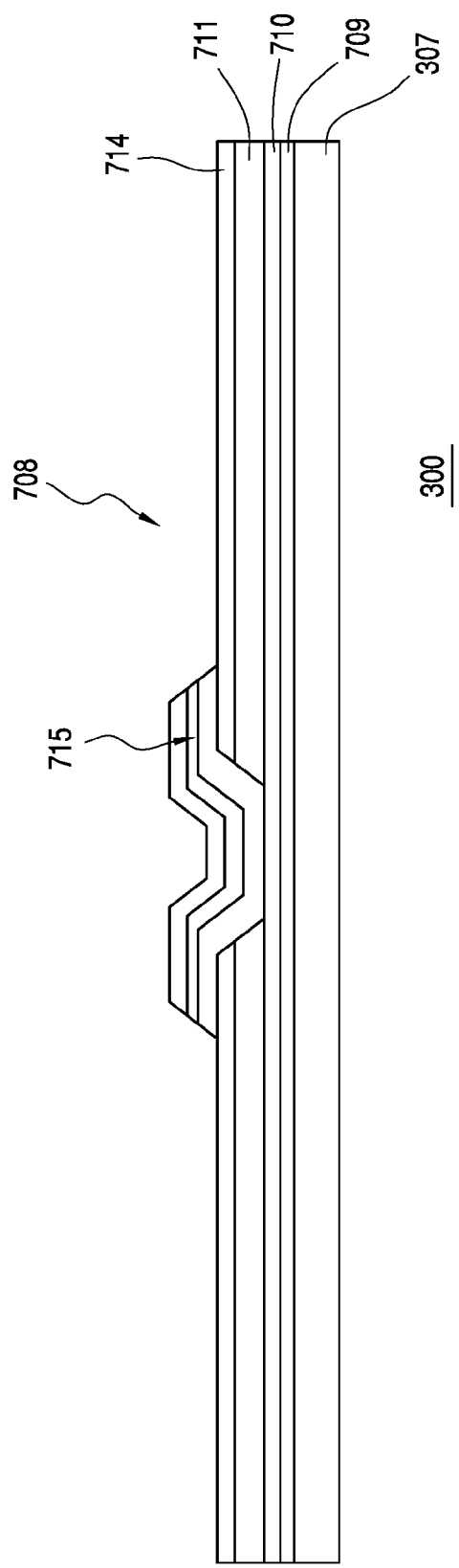
FIG. 8 illustrates a partial cross-sectional view of the electronic device of FIG. 3 in a gate contact build area of the electronic device after providing the semiconductor device layer(s) over the substrate assembly.

Turning ahead in the drawings, FIG. 7 illustrates a partial cross-sectional view of electronic device 300 in a device build area of electronic device 300 after providing one or more semiconductor device layers 708 over substrate assembly 307, according to the embodiment of FIG. 3. For example, first passivation layer 709 is provided over substrate assembly 307, gate layer 710 is provided over first passivation layer 709, first dielectric layer 711 is provided over gate layer 710, one or more active layers 712 are provided over first dielectric layer 711, second dielectric layer 713 is provided over active layer(s) 712, second passivation layer 714 is provided over second dielectric layer 713, contact layer(s) 715 are provided over active layer(s) 712 and gate layer 710, and device layer(s) 716 are provided over contact layer(s) 715 and second passive layer 714. Meanwhile, FIG. 8 illustrates a partial cross-sectional view of electronic device 300 in a gate contact build area of electronic device 300 after providing the semiconductor device layer(s) 708 over substrate assembly 307, according to the embodiment of FIG. 3. Here, first passivation layer 709 is provided over substrate assembly 307, gate layer 710 is provided over first passivation layer 709, first dielectric layer 711 is provided over gate layer 710, and second passivation layer 714 is provided over first dielectric layer 711, and contact layer(s) 715 are provided over gate layer 710. In these or other embodiments, semiconductor layer(s) 708 can be similar or identical to the semiconductor layer(s) of method 100 (FIG. 1). Accordingly, first passivation layer 709 can be similar or identical to the first passivation layer of activity 501 (FIG. 5), gate layer 710 can be similar or identical to the gate layer of activity 502 (FIG. 5), first dielectric layer 711 can be similar or identical to the first dielectric layer of activity 503 (FIG. 5), active layer(s) 712 can be similar or identical to the active layer(s) of activity 504 (FIG. 5), second dielectric layer 713 can be similar or identical to the second dielectric layer of activity 505 (FIG. 5), second passivation layer 714 can be similar or identical to the second passivation layer of activity 506 (FIG. 5), contact layer(s) 715 can be similar or identical to the contact layer(s) of activity 507 (FIG. 5), and device layer(s) 716 can be similar or identical to the device layer(s) of activity 508 (FIG. 5).

Turning now back to FIG. 4, the semiconductor device layer(s) can be provided (e.g., deposited) over part or substantially all of the second side of the device substrate. For example, in many embodiments, when the active sections of activity 104 (FIG. 1) are provided by removing (e.g., etching) excess active section material, the semiconductor device layer(s) can be provided (e.g., deposited) over substantially all of the second side of the device substrate. Alternatively, when the active sections of activity 104 (FIG. 1) are provided by selective deposition, the semiconductor device layer(s) can be provided (e.g., deposited) over only select parts of the second side of the device substrate.

Notably, whether the semiconductor device layer(s) are deposited over substantially all or only part of the second side of the device substrate, in many embodiments, a perimeter region of the second side of the device substrate can remain devoid of the semiconductor layer(s) to ensure that the material(s) provided for the semiconductor layers are not provided on the equipment handling the carrier substrate of method 100 (FIG. 1). The size (e.g., surface area, width, etc.) of the perimeter region can depend on the equipment and/or techniques used to provide the semiconductor device layer(s) over the second side of the device substrate. That is, the equipment and techniques can determine the accuracy of the deposition.

Meanwhile, when the active sections of activity 104 (FIG. 1) are provided by removing (e.g., etching) excess active section material, for reference purposes, the semiconductor device layer(s) can be said to comprise a first portion and a second portion. As explained in greater detail as follows, the first portion of the semiconductor layer(s) can represent the portion of the semiconductor layer(s) that is partially or completely removed, and the second portion of the semiconductor layer(s) can represent the portion of the semiconductor layer(s) that remain as part of the active sections of activity 104 of method 100 (FIG. 1).

Accordingly, activity 104 can comprise activity 402 of removing (e.g., etching) part or all of the first portion of the semiconductor device layer(s) from over the second side of the device substrate and leaving the second portion of the semiconductor device layer(s) remaining over the second side of the device substrate such that the active sections comprise the second portion of the semiconductor device layer(s). In some embodiments, activity 402 can be performed as one or more removal (e.g., etching) activities to remove the part or the all of the first portion of the semiconductor device layer(s). When activity 402 is implemented with one or more etching activities, in many embodiments, at least one of the one or more etching activities can be a timed etch.

For example, in many embodiments, activity 402 can comprise an activity of plasma etching the part or the all of the first portion of the semiconductor device layer(s) and/or an activity of wet etching the part or the all of the first portion of the semiconductor device layer(s). In these or other embodiments, the plasma etching can be fluorine based and/or the wet etching can be hydrofluoric-acid based. In many embodiments, the plasma etching activity can be performed before the wet etching activity. Further, the plasma etch activity can be timed and/or can anisotropically remove most of the part or the all of the first portion of the semiconductor device layer(s), and/or the wet etch activity can be shorter in time than the plasma etch activity and/or can be configured to remove the part or the all of the first portion of the semiconductor device layer(s) faster (e.g., substantially faster) than it removes the device substrate (e.g., to prevent the device substrate from being removed while ensuring the desired part or all of the first portion of the semiconductor device layer(s) is removed).

In many embodiments, the first portion of the semiconductor device layer(s) can occupy a first volume and the second portion of the semiconductor device layer(s) can occupy a second volume over the second side of the device substrate. The first volume and the second volume can be related in a volumetric ratio. In many embodiments, the volumetric ratio of the first volume to the second volume can be less than or equal to approximately 0.9. Further, in these or other embodiments, the volumetric ratio of the first volume to the second volume can be greater than or equal to approximately 0.005, 0.01, 0.02, 0.05, 0.08, and/or 0.1.

Further, activity 104 can comprise activity 403 of forming (e.g., etching) one or more interconnect vias over the contact layer(s). In some embodiments, activity 403 can be performed as one or more removal (e.g., etching) activities to form the interconnect via(s) over the contact layer(s). For example, in some embodiments, the interconnect via(s) can be formed through the device layer(s), thereby exposing a surface of the top most contact layer(s). When the interconnect via(s) are formed by etching (e.g., anisotropic etching), in many embodiments, the etch can be performed using a plasma etchant (e.g., a fluorine-based plasma etchant) or a wet etchant. In some embodiments, activity 403 can be performed as part of activity 402, and vice versa. In further embodiments, activity 402 and activity 403 can be performed approximately simultaneously, or sequentially, as desirable.

Returning now to FIG. 1, in many embodiments, method 100 can comprise activity 105 of providing one or more interconnects over the second side of the device substrate to electrically couple together the active sections. The interconnect(s) each can comprise a conductive material. For example, the conductive material can comprise metal (e.g., cracked gold). In these or other embodiments, the interconnect(s) each can comprise a wavy architecture (e.g., a spring-like architecture), such as, for example, with respect to a plane approximately parallel to the x-y plane of the device substrate and/or with respect to a plane approximately perpendicular to the x-y plane of the device substrate.

In these or other embodiments, the interconnect(s) can be configured to be reversibly expanded and/or contracted, such as, for example, when the electronic device is deformed and/or when the device substrate is decoupled from the carrier substrate, as discussed below. Accordingly, unlike straight metal interconnect(s), which may break when stretched and/or compressed, such wavy metal interconnects can electrically couple the active sections together while also permitting the electronic device to deform (e.g., flex and/or stretch). Generally, providing the wavy architecture parallel to the x-y plane of the device substrate can permit deformation of the electronic device of a type corresponding to a bowing and/or distortion of the device substrate, and providing the wavy architecture perpendicular to the x-y plane of the device substrate can permit deformation of the electronic device of a type that corresponding to a bowing and/or warping of the device substrate, as these concepts are described above.

Exemplary wave architectures can comprise any suitable wave form (e.g., a curved wave form, such as, for example, a sinusoidal wave form, a triangular wave form, a saw tooth wave form, a square wave form, etc.). Further, curved wave forms can comprise any suitable amount of curvature. Further still, the wave architectures can have a constant or non-constant wave pattern, and/or the interconnects can have the same or different wave architectures as each other when multiple interconnects are implemented.

Figure 9:
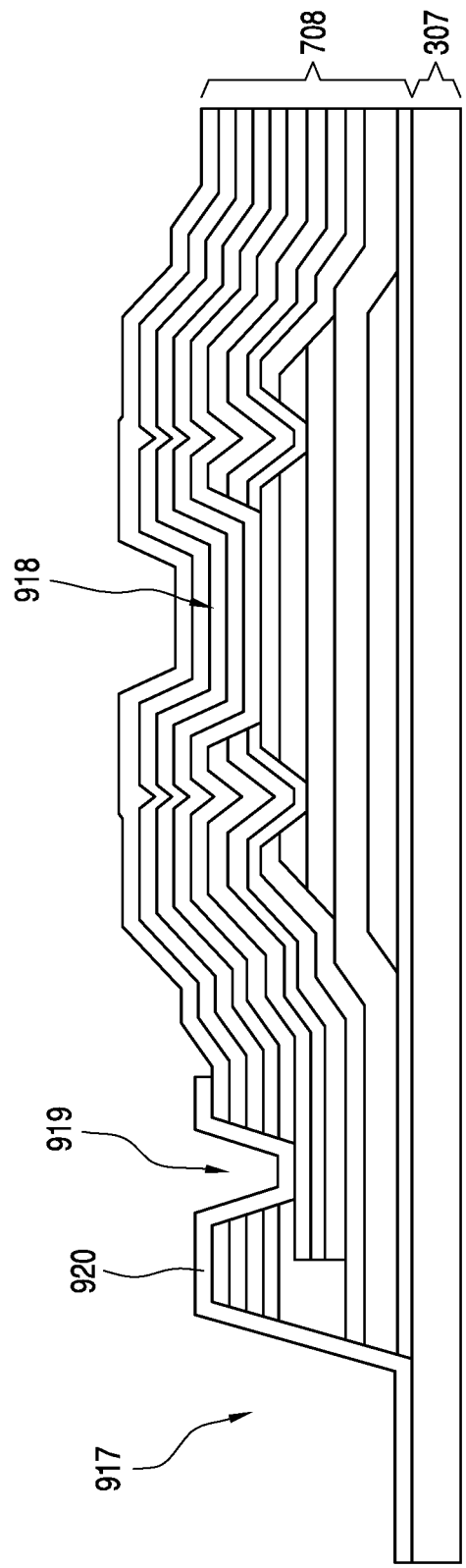
FIG. 9 illustrates a partial cross-sectional view of the electronic device of FIG. 3 in the device build area of the electronic device after removing (e.g., etching) all of a first portion of semiconductor device layer(s) from over the substrate assembly and leaving a second portion of the semiconductor device layer(s) remaining over the substrate assembly, after forming an interconnect via, and after providing an interconnect over the substrate assembly.

Turning ahead in the drawings, FIG. 9 illustrates a partial cross-sectional view of electronic device 300 in the device build area of electronic device 300 after removing (e.g., etching) all of a first portion 917 of semiconductor device layer(s) 708 from over substrate assembly 307 and leaving a second portion 918 of semiconductor device layer(s) 708 remaining over substrate assembly 307, after forming an interconnect via 919, and after providing interconnect 920 over substrate assembly 307. In these or other embodiments, first portion 917 can be similar or identical to the first portion of the semiconductor device layer(s) of activity 401 (FIG. 4), second portion 918 can be similar or identical to the second portion of activity 401 (FIG. 4), and interconnect 920 can be similar or identical to the interconnect(s) of method 100 (FIG. 1).

Returning again to FIG. 1, in some embodiments, method 100 can comprise activity 106 of providing a sacrificial layer over the second side of the device substrate and the active sections. In some embodiments, activity 106 can comprise an activity of coupling (e.g., removably coupling) the sacrificial layer to the second side of the device substrate and the active sections. In further embodiments, such as, for example, when activity 109 (below) is performed, activity 106 can comprise an activity of coupling (e.g., removably coupling) the sacrificial layer to the second elastomeric layer of activity 109.

In general, activity 106 can be performed after activities 101-105. In some embodiments, the sacrificial layer can be similar to a backing strip on an adhesive bandage. Accordingly, in many embodiments, the sacrificial layer can be selectively removed (e.g., peeled) from the electronic device when a user is ready to deploy the electronic device.

In these or other embodiments, the sacrificial layer can support the device substrate both while and after activity 107 is performed. The sacrificial layer can permit the electronic device to be more easily coupled to the surface of an object (e.g., organic tissue, consumables, etc.) without damaging the electronic device or crumpling the electronic device. Still, in some embodiments, activity 106 can be omitted.

In many embodiments, method 100 can comprise activity 107 of decoupling (e.g., debonding) the device substrate and the active sections from the carrier substrate. In some embodiments, when activity 106 is performed, activity 107 can be performed after activity 106. Meanwhile, as explained in greater detail below, when activity 108 (below) is performed, activity 107 can be performed before activity 108, and when activity 109 (below) is performed, activity 107 can be performed after activity 109.

For example, in some embodiments, performing activity 107 can comprise an activity of applying a release force (e.g., a steady release force) to the device substrate to decouple the device substrate and the active sections from the carrier substrate. In many embodiments, the release force can be applied to the device substrate (e.g., by hand). In these or other embodiments, the release force can be applied (or augmented) by inserting a blade under the device substrate and pressing on the device substrate in a direction away from the carrier substrate.

Further, in these or other embodiments, activity 107 can comprise an activity of severing the device substrate from the carrier substrate, such as, for example, using any suitable cutting implement (e.g., a blade, a laser, etc.). The activity of severing the device substrate from the carrier substrate can be performed alternatively to or as part of the activity of applying the release force to the device substrate.

In many embodiments, maintaining an angle of less than or equal to approximately 45 degrees between the device substrate and the carrier substrate when performing activity 107 can mitigate or prevent damage to the active section(s).

In some embodiments, activity 107 can be performed without first lowering the device substrate-carrier substrate coupling strength, such as, for example, using chemical or optical decoupling procedures (e.g., electronics on plastic by laser release (EPLaR™), surface free technology by laser annealing/ablation (SUFTLA™), etc.). In these embodiments, by avoiding using chemical or optical decoupling procedures (e.g., electronics on plastic by laser release (EPLaR™), surface free technology by laser annealing/ablation (SUFTLA™), etc.), device defects of the semiconductor device layer(s) and/or decreased semiconductor device yield that can result from using such chemical or optical debonding procedures can be reduced or eliminated. For example, optical decoupling procedures can damage the semiconductor device layer(s) through heat distortion and/or formation of particulate debris. Meanwhile, chemical decoupling procedures can damage the semiconductor device layer(s) by exposing the semiconductor device layer(s) to the chemical(s), resulting in degradation of the semiconductor device layer(s). Moreover, using chemical debonding procedures may require subsequent cleaning to remove any residual chemicals from the semiconductor device layer(s) and/or may not permit the device substrate to be kept approximately flat during decoupling because physically constraining the device substrate while immersing the device substrate in chemicals can be challenging. However, in other embodiments, the device substrate-carrier substrate coupling strength can be lowered as part of activity 107, such as, for example, when activity 104 and/or activity 401 (FIG. 4) is performed using the EPLaR™ manufacturing techniques described above.

In some embodiments, method 100 can comprise activity 108 of providing a first elastomeric layer over the first side of the device substrate. In these or other embodiments, the first elastomeric layer can comprise an elastomeric material (e.g., polydimethylsiloxane (PDMS)). In some embodiments, performing activity 108 can comprise an activity of coupling the first elastomeric layer to the first side of the device substrate. In other embodiments, activity 108 can be omitted.

In some embodiments, method 100 can comprise activity 109 of providing a second elastomeric layer over the second side of the device substrate and the active sections. In these or other embodiments, the second elastomeric layer can comprise the elastomeric material (e.g., PDMS). In some embodiments, performing activity 109 can comprise an activity of coupling the second elastomeric layer to the second side of the device substrate. In other embodiments, activity 109 can be omitted.

Implementing the electronic device of method 100 with the first elastomeric layer of activity 108 and/or the second elastomeric layer of activity 109 can increase the stretchability of the electronic device. In many embodiments, activity 108 and/or activity 109 are performed after activities 101-105 because the elastomeric material (e.g., PDMS) may not be able to withstand the manufacturing conditions of activities 101-105. For example, PDMS, which has a maximum processing temperature of approximately 100° C., cannot withstand conventional manufacturing conditions for flat panel electronic displays, which may include temperatures exceeding approximately 300° C. to approximately 350° C. and may include corrosive chemicals.

In various embodiments, method 100 can comprise activity 110 of providing an adhesive layer over one of the first side of the device substrate, the second side of the device substrate, the first elastomeric layer, or the second elastomeric layer. The adhesive layer can comprise a temporary medical adhesive and can be configured to aid in coupling the electronic device to an object (e.g., organic tissue, etc.), such as, for example, when electronic device is implemented as a smart bandage. Activity 110 can be performed before activity 106, before or after activity 108, and/or before or after activity 109, as applicable. In other embodiments, activity 110 can be omitted.

Figure 10:
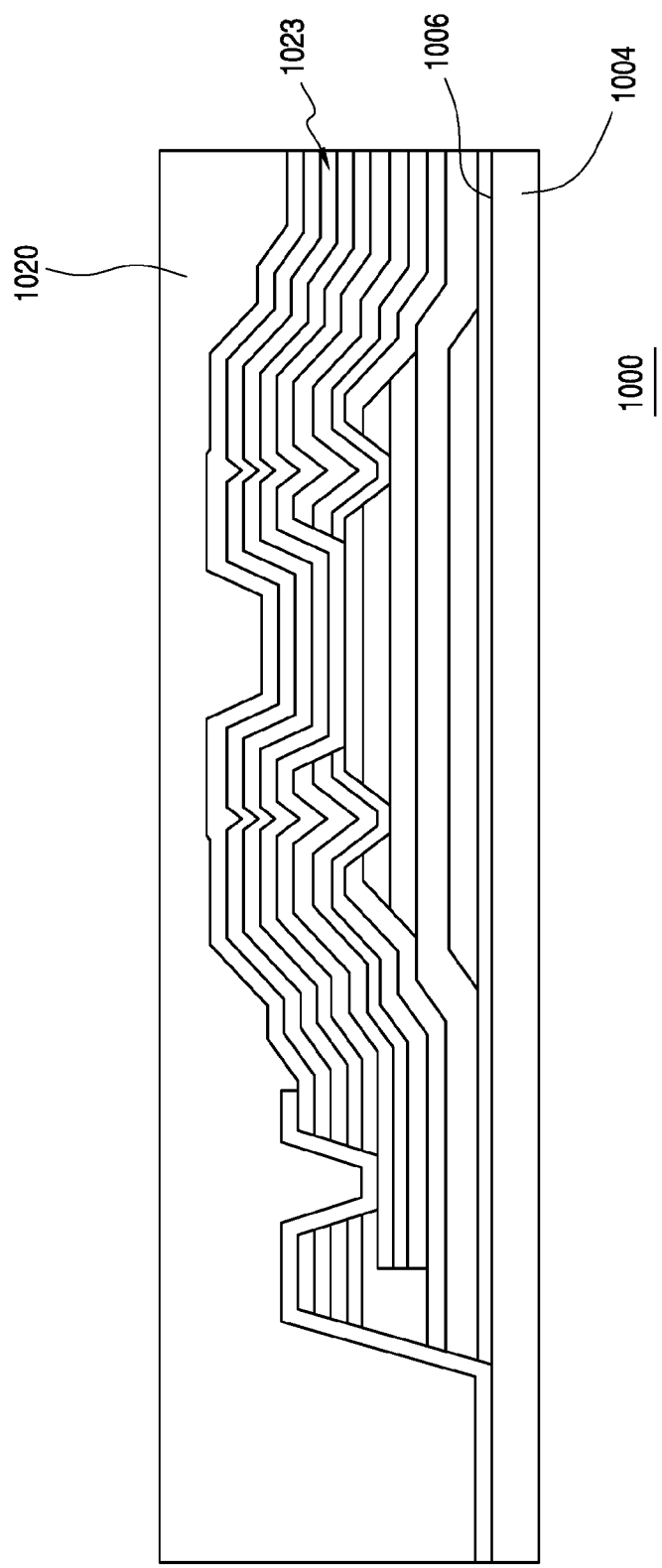
FIG. 10 illustrates a partial cross-sectional view of an electronic device in a device build area of the electronic device with a sacrificial layer of the electronic device coupled to a second side of a device substrate of the electronic device, according to an embodiment.

Turning ahead in the drawings, FIG. 10 illustrates a partial cross-sectional view of an electronic device 1000 in a device build area of electronic device 1000 with a sacrificial layer 1020 of electronic device 1000 coupled to a second side 1006 of a device substrate 1004 of electronic device 1000 and an active section 1023 of electronic device 1000, according to an embodiment. Electronic device 1000 can be similar or identical to electronic device 300 (FIGS. 3, 6, 7, & 9). Sacrificial layer 1020 can be similar or identical to the sacrificial layer described above with respect to activity 106 (FIG. 1). Further, device substrate 1004 can be similar or identical to device substrate 304 (FIG. 3) and/or the device substrate described above with respect to activity 101 (FIG. 1); and second side 1006 can be similar or identical to second side 306 and/or the second side of the device substrate described above with respect to method 100 (FIG. 1). Also, active section 1023 can be similar or identical to one of the active sections described above with respect to method 100 (FIG. 1).

Figure 11:
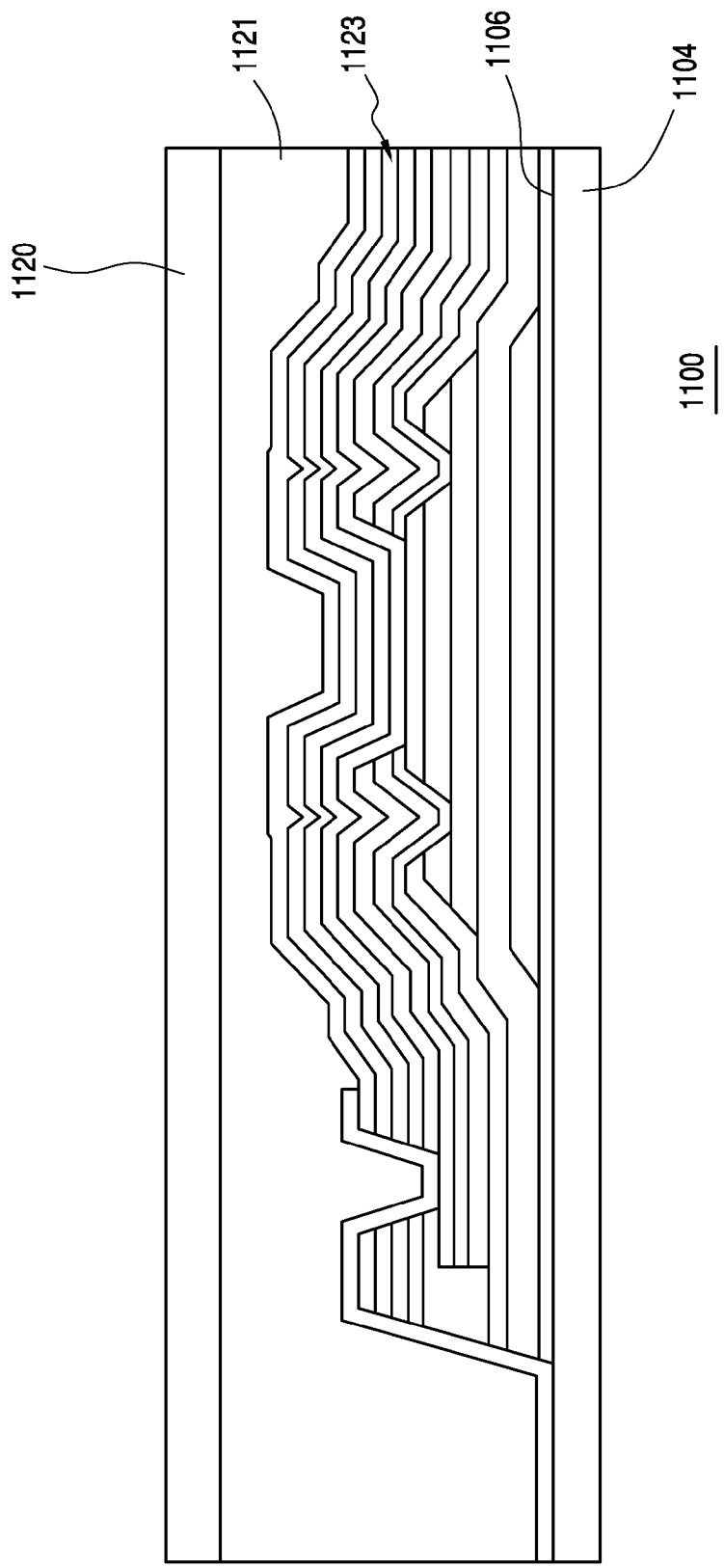
FIG. 11 illustrates a partial cross-sectional view of an electronic device in a device build area of the electronic device with an elastomeric layer of the electronic device coupled to a second side of a device substrate of the electronic device and a sacrificial layer of the electronic device coupled to the elastomeric layer, according to an embodiment.

Meanwhile, FIG. 11 illustrates a partial cross-sectional view of an electronic device 1100 in a device build area of electronic device 1100 with an elastomeric layer 1121 of electronic device 1100 coupled to a second side 1106 of a device substrate 1104 of electronic device 1100 and an active section 1123 of electronic device 1100, and a sacrificial layer 1120 of electronic device 1000 coupled to elastomeric layer 1121, according to an embodiment. Electronic device 1100 can be similar or identical to electronic device 300 (FIGS. 3, 6, 7, & 9) and/or electronic device 1000 (FIG. 10). Sacrificial layer 1120 can be similar or identical to the sacrificial layer described above with respect to activity 106 (FIG. 1) and/or sacrificial layer 1020 (FIG. 10). Elastomeric layer 1121 can be similar or identical to the second elastomeric layer described above with respect to activity 108 (FIG. 1). Further, device substrate 1004 can be similar or identical to device substrate 304 (FIG. 3), device substrate 1004 (FIG. 10), and/or the device substrate described above with respect to activity 101 (FIG. 1); and second side 1006 can be similar or identical to second side 306, second side 1006 (FIG. 10) and/or the second side of the device substrate described above with respect to method 100 (FIG. 1). Also, active section 1123 can be similar or identical to one of the active sections described above with respect to method 100 (FIG. 1) and/or active section 1023 (FIG. 10).

Figure 12:
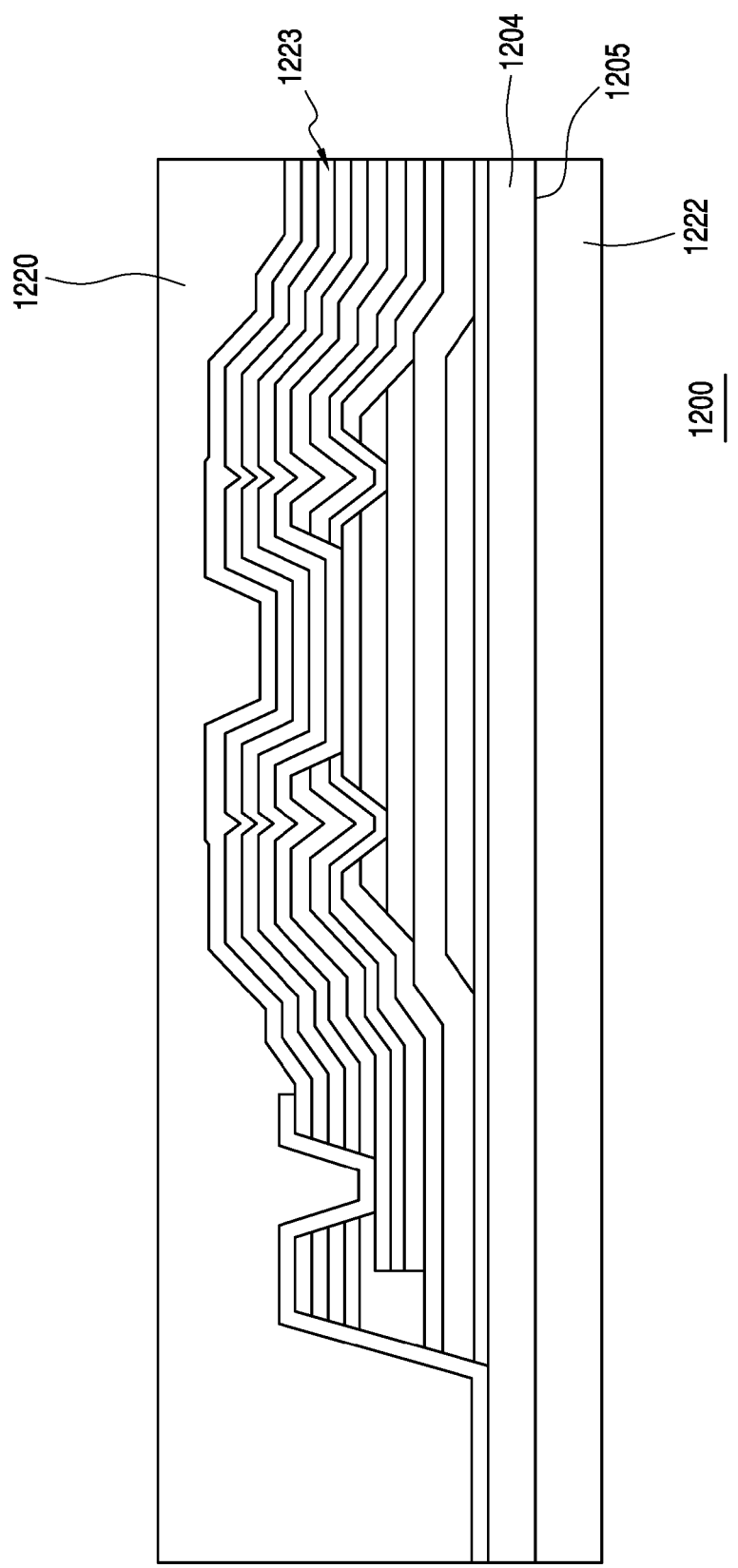
FIG. 12 illustrates a partial cross-sectional view of an electronic device in a device build area of the electronic device with an elastomeric layer of the electronic device coupled to a first side of a device substrate of the electronic device and a sacrificial layer of the electronic device coupled to a second side of the device substrate, according to an embodiment.

Further, FIG. 12 illustrates a partial cross-sectional view of an electronic device 1200 in a device build area of electronic device 1200 with an elastomeric layer 1222 of electronic device 1200 coupled to a first side 1205 of a device substrate 1204 of electronic device 1200 and a sacrificial layer 1220 of electronic device 1200 coupled to a second side 1206 of device substrate 1204 and an active section 1223 of electronic device 1200, according to an embodiment. Electronic device 1200 can be similar or identical to electronic device 300 (FIGS. 3, 6, 7, & 9), electronic device 1000 (FIG. 10) and/or electronic device 1100 (FIG. 11). Sacrificial layer 1220 can be similar or identical to the sacrificial layer described above with respect to activity 106 (FIG. 1), sacrificial layer 1020 (FIG. 10) and/or sacrificial layer 1120 (FIG. 11). Elastomeric layer 1222 can be similar or identical to the first elastomeric layer described above with respect to activity 108 (FIG. 1). Further, device substrate 1204 can be similar or identical to device substrate 304 (FIG. 3), device substrate 1004 (FIG. 10), device substrate 1104 (FIG. 11) and/or the device substrate described above with respect to activity 101 (FIG. 1); second side 1006 can be similar or identical to second side 306, second side 1006 (FIG. 10), second side 1106 (FIG. 11), and/or the second side of the device substrate described above with respect to method 100 (FIG. 1); and first side 1205 can be similar or identical to first side 305 (FIG. 3) and/or the first side of the device substrate described above with respect to method 100 (FIG. 1). Also, active section 1223 can be similar or identical to one of the active sections described above with respect to method 100 (FIG. 1), active section 1023 (FIG. 10), and/or active section 1123 (FIG. 11).

Figure 13:
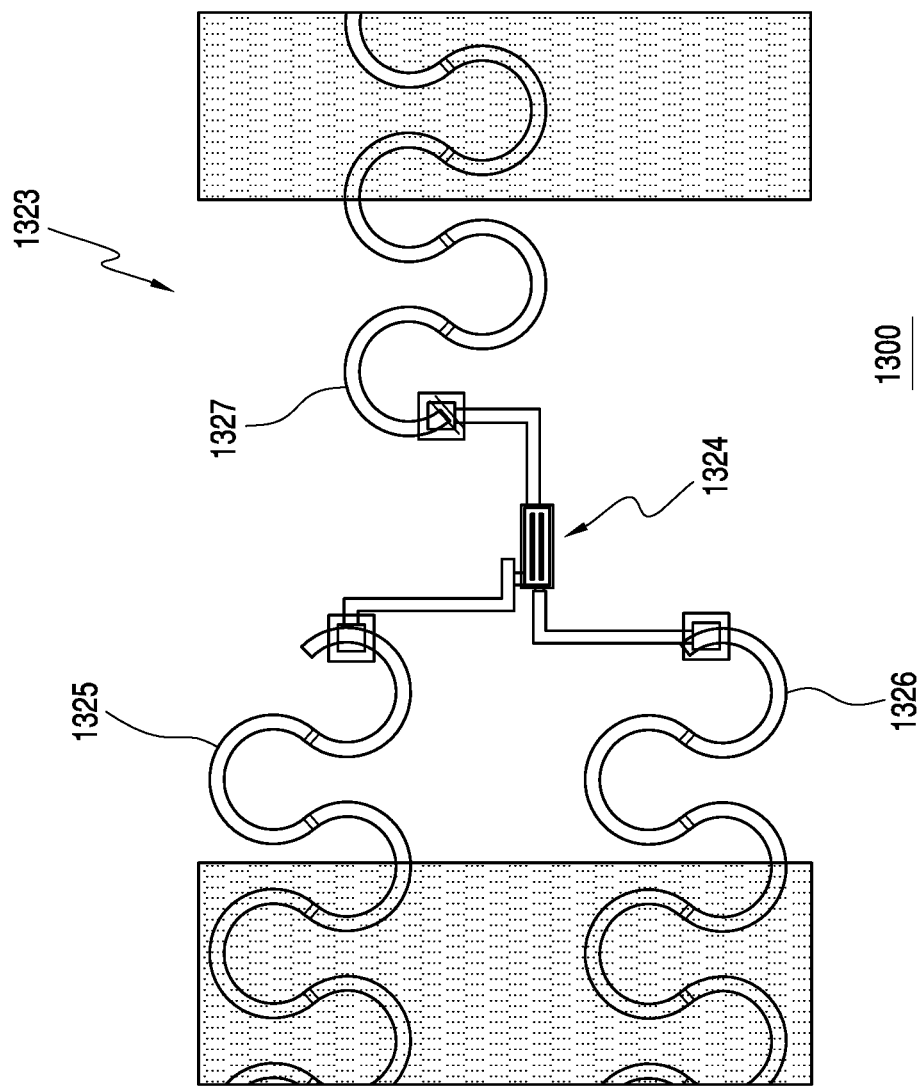
FIG. 13 illustrates a partial top view of an electronic device including an active section having a semiconductor device coupled to three interconnects, according to an embodiment.

Further still, FIG. 13 illustrates a partial top view of an electronic device 1300 including an active section 1323 having a semiconductor device 1324 coupled to interconnect 1325, interconnect 1326, and interconnect 1327, according to an embodiment. Electronic device 1300 can be similar or identical to electronic device 300 (FIGS. 3, 6, 7, & 9), electronic device 1000 (FIG. 10), electronic device 1100 (FIG. 11), and/or electronic device 1200 (FIG. 12). Semiconductor device 1324 can be similar or identical to the semiconductor device(s) described above with respect to method 100 (FIG. 1), and interconnects 1325-1327 each can be similar or identical to the interconnect(s) described above with respect to method 100 (FIG. 1) and/or interconnect 919 (FIG. 9). Also, active section 1323 can be similar or identical to one of the active sections described above with respect to method 100 (FIG. 1), active section 1023 (FIG. 10), active section 1123 (FIG. 11), and/or active section 1223 (FIG. 12).

Figure 14:
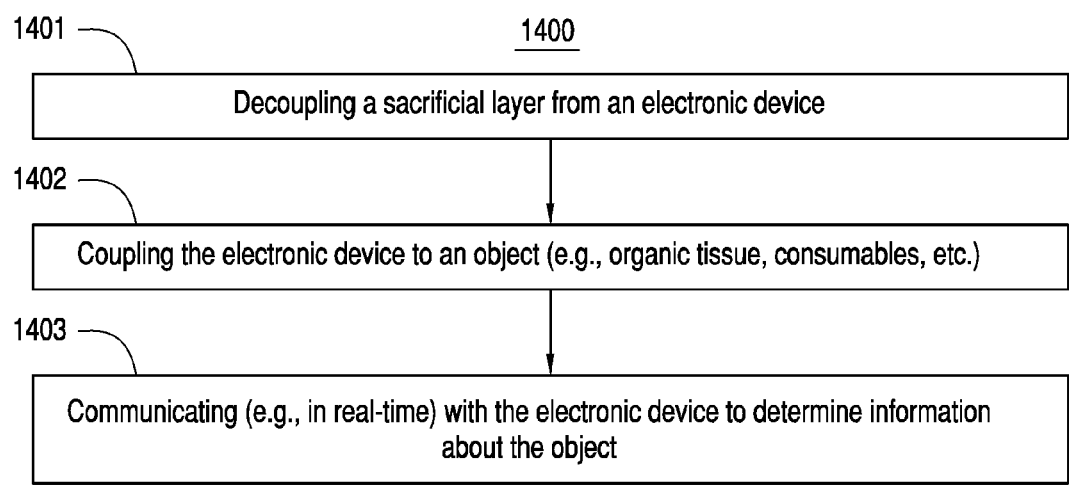
FIG. 14 illustrates an example of a method, according to an embodiment.

Turning ahead in the drawings, FIG. 14 illustrates an example of a method 1400, according to an embodiment. Method 1400 is merely exemplary and is not limited to the embodiments presented herein. Method 1400 can be employed in many different embodiments or examples not specifically depicted or described herein. In some embodiments, the activities of method 1400 can be performed in the order presented. In other embodiments, the activities of method 1400 can be performed in any other suitable order. In still other embodiments, one or more of the activities in method 1400 can be combined or skipped.

Method 1400 can comprise activity 1401 of decoupling a sacrificial layer from an electronic device. The electronic device can be similar or identical to electronic device 300 (FIGS. 3, 6, 7, & 9), electronic device 1000 (FIG. 10), electronic device 1100 (FIG. 11), electronic device 1200 (FIG. 12), and/or electronic device 1300 (FIG. 13). Further, the sacrificial layer can be similar or identical to the sacrificial layer described above with respect to activity 106 (FIG. 1), sacrificial layer 1020 (FIG. 10), sacrificial layer 1120 (FIG. 11), and/or sacrificial layer 1220 (FIG. 12). In some embodiments, activity 1401 can be omitted.

Further, method 1400 can comprise activity 1402 of coupling the electronic device to an object (e.g., organic tissue, consumables, etc.). In many embodiments, activity 1402 can be performed after activity 1401.

Further still, method 1400 can comprise activity 1403 of communicating (e.g., in real-time) with the electronic device to determine information about the object. In some embodiments, activity 1403 can be performed while the electronic device is coupled to the object. In many embodiments, when the object is organic tissue, activity 1403 can be performed to detect and/or diagnose multiple diseases of an organism having the organic tissue with clinical level sensitivity. In various embodiments, activity 1403 can be performed using any suitable mechanisms (e.g., a computer, an antenna, etc.) and medium (e.g., Bluetooth, Near Field Communication, Wi-Fi, a cable, a bus, etc.) for communication (e.g., wired or wireless communication) with the electronic device.

Although the invention has been described with reference to specific embodiments, it will be understood by those skilled in the art that various changes can be made without departing from the spirit or scope of the invention. Accordingly, the disclosure of embodiments is intended to be illustrative of the scope of the invention and is not intended to be limiting. It is intended that the scope of the invention shall be limited only to the extent required by the appended claims. To one of ordinary skill in the art, it will be readily apparent that the semiconductor device and its methods of providing the semiconductor device discussed herein may be implemented in a variety of embodiments, and that the foregoing discussion of certain of these embodiments does not necessarily represent a complete description of all possible embodiments. Rather, the detailed description of the drawings, and the drawings themselves, disclose at least one preferred embodiment, and may disclose alternative embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A method of providing an electronic device, the method comprising:
   providing a carrier substrate;
   providing a device substrate comprising a first side and a second side opposite the first side, the device substrate comprising a flexible substrate;
   coupling the first side of the device substrate to the carrier substrate;
   after coupling the first side of the device substrate to the carrier substrate, providing two or more device island sections over the second side of the device substrate, each device island section of the two or more device island sections being spatially separate from each other and comprising at least one semiconductor device; and
   providing one or more wavy metal interconnects over the second side of the device substrate to electrically couple together the two or more device island sections, the one or more wavy metal interconnects being configured to be at least one of reversibly expanded or reversibly contracted.

2. The method of claim 1 wherein:
   providing the two or more device island sections over the second side of the device substrate comprises:
      after coupling the first side of the device substrate to the carrier substrate, providing one or more semiconductor device layers over the second side of the device substrate, the one or more semiconductor device layers comprising a first portion and a second portion; and
      removing part or all of the first portion of the one or more semiconductor device layers from over the second side of the device substrate and leaving the second potion of the one or more semiconductor device layers remaining over the second side of the device substrate such that the two or more device island sections comprise the second portion of the one or more semiconductor device layers.

3. The method of claim 2 wherein:
   removing part or all of the first portion of the one or more semiconductor device layers from over the second side of the device substrate and leaving the second portion of the one or more semiconductor device layers remaining over the second side of the device substrate comprises:
      etching the part or the all of the first portion of the one or more semiconductor device layers from over the second side of the device substrate.

4. The method of claim 3 wherein at least one of:
   a volumetric ratio of the first portion of the one or more semiconductor device layers to the second portion of the one or more semiconductor device layers is less than or equal to approximately 0.9; or
   the volumetric ratio of the first portion of the one or more semiconductor device layers to the second portion of the one or more semiconductor device layers is greater than or equal to approximately 0.1.

5. The method of claim 2 wherein:
   providing the one or more semiconductor device layers over the second side of the device substrate comprises:
      providing a first passivation layer over the second side of the device substrate, the first passivation layer comprising silicon nitride;
      providing a gate layer over the first passivation layer, the gate layer comprising a conductive material;
      providing a first dielectric layer over the gate layer, the first dielectric layer comprising silicon nitride;
      providing one or more active layers over the first dielectric layer;
      providing a second dielectric layer over the one or more active layers, the second dielectric layer comprising silicon nitride;
      providing a second passivation layer over at least one of the one or more active layers or the gate layer, the second passivation layer comprising silicon nitride;
      providing one or more contact layers over the at least one of the one or more active layers or the gate layer; and
      providing one or more device layers over at least one of the one or more contact layers or the second passivation layer.

6. The method of claim 5 further comprising:
   forming one or more interconnect vias over the one or more contact layers;

wherein:
the forming the one or more interconnect vias over the one or more contact layers occurs approximately simultaneously with the removing the part or the all of the first portion of the one or more semiconductor device layers from over the second side of the device substrate and leaving the second portion of the one or more semiconductor device layers remaining over the second side of the device substrate such that the two or more device island sections comprise the second portion of the one or more semiconductor device layers.

7. The method of claim 2 wherein at least one of:
the carrier substrate comprises a rigid substrate, the carrier substrate comprising at least one of alumina, silicon, glass, stainless steel, or sapphire;
the carrier substrate is CTE matched to the device substrate;
the device substrate comprises at least one of polyethylene naphthalate, polyethylene terephthalate, polyethersulfone, polyimide, polycarbonate, cyclic olefin copolymer, or liquid crystal polymer;
the device substrate comprises an elastic modulus of less than approximately five GigaPascals;
or
the device substrate comprises a thickness of greater than or equal to approximately 1 micrometer and less than or equal to approximately 1 millimeter.

8. The method of claim 1 further comprising:
after providing the two or more device island sections over the second side of the device substrate, decoupling the device substrate and the two or more device island sections from the carrier substrate.

9. The method of claim 8 further comprising:
after providing the two or more device island sections over the second side of the device substrate and before decoupling the device substrate and the two or more device island sections from the carrier substrate, providing a sacrificial layer over the second side of the device substrate and the two or more device island sections; and
after decoupling the device substrate and the two or more device island sections from the carrier substrate, providing an elastomeric layer over the first side of the device substrate.

10. The method of claim 1 further comprising:
after providing the two or more device island sections over the second side of the device substrate, providing a sacrificial layer over the second side of the device substrate and the two or more device island sections; and
after providing the two or more device island sections over the second side of the device substrate, decoupling the device substrate and the two or more device island sections from the carrier substrate.

11. The method of claim 1 further comprising:
after providing the two or more device island sections over the second side of the device substrate, providing an elastomeric layer over the second side of the device substrate and the two or more device island sections; and
after providing the elastomeric layer over the second side of the device substrate and the two or more device island sections, providing a sacrificial layer over the elastomeric layer.

12. The method of claim 1 wherein:
providing the two or more device island sections over the second side of the device substrate comprises:
after coupling the first side of the device substrate to the carrier substrate, providing one or more semiconductor device layers over the second side of the device substrate, the one or more semiconductor device layers comprising a first portion and a second portion; and
removing part or all of the first portion of the one or more semiconductor device layers from over the second side of the device substrate and leaving the second potion of the one or more semiconductor device layers remaining over the second side of the device substrate such that the two or more device island sections comprise the second portion of the one or more semiconductor device layers;
removing part or all of the first portion of the one or more semiconductor device layers from over the second side of the device substrate and leaving the second portion of the one or more semiconductor device layers remaining over the second side of the device substrate comprises:
etching the part or the all of the first portion of the one or more semiconductor device layers from over the second side of the device substrate;
the device substrate comprises polyimide; and
the method further comprises:
providing one or more wavy metal interconnects over the second side of the device substrate to electrically couple together the two or more device island sections.

13. The method of claim 12 further comprising:
after providing the two or more device island sections over the second side of the device substrate, decoupling the device substrate and the two or more device island sections from the carrier substrate.

* * * * *